United States Patent
Redmann

(10) Patent No.: US 8,343,012 B2
(45) Date of Patent: *Jan. 1, 2013

(54) DEVICE AND METHOD FOR EXERCISE PRESCRIPTION, DETECTION OF SUCCESSFUL PERFORMANCE, REPORTING, AND PROVISION OF REWARD THEREFORE

(76) Inventor: William Gibbens Redmann, Glendale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/359,505

(22) Filed: Jan. 27, 2012

(65) Prior Publication Data

US 2012/0129138 A1 May 24, 2012

Related U.S. Application Data

(63) Continuation of application No. 10/901,266, filed on Jul. 28, 2004, now Pat. No. 8,109,858.

(51) Int. Cl.
*A63B 71/00* (2006.01)
*G09B 19/00* (2006.01)

(52) U.S. Cl. .................. 482/8; 482/9; 434/236

(58) Field of Classification Search .......... 482/1–9; 273/444, 441; 463/1; 434/247–257
See application file for complete search history.

(56) References Cited

U.S. PATENT DOCUMENTS

| | | | | |
|---|---|---|---|---|
| 4,337,049 A * | 6/1982 | Connelly | ...................... | 434/247 |
| 4,763,284 A * | 8/1988 | Carlin | ............................. | 702/41 |
| 5,524,637 A * | 6/1996 | Erickson | ...................... | 600/592 |
| 5,694,340 A * | 12/1997 | Kim | .............................. | 702/141 |
| 5,733,193 A * | 3/1998 | Allard et al. | ...................... | 463/8 |
| 5,833,549 A * | 11/1998 | Zur et al. | ...................... | 473/199 |
| 5,957,812 A * | 9/1999 | Harrigan | .......................... | 482/8 |
| 6,059,576 A * | 5/2000 | Brann | .......................... | 434/247 |
| 6,152,856 A * | 11/2000 | Studor et al. | ...................... | 482/8 |
| 6,183,365 B1 * | 2/2001 | Tonomura et al. | ............. | 463/36 |
| 6,190,287 B1 * | 2/2001 | Nashner | ........................... | 482/8 |
| 6,334,837 B1 * | 1/2002 | Hein et al. | ...................... | 482/8 |
| 6,397,151 B1 * | 5/2002 | Yamagishi et al. | ............. | 702/41 |
| 6,422,945 B1 * | 7/2002 | Okita et al. | ..................... | 463/49 |
| 6,554,706 B2 * | 4/2003 | Kim et al. | ....................... | 463/36 |
| 6,585,622 B1 * | 7/2003 | Shum et al. | ...................... | 482/8 |
| 6,623,358 B2 * | 9/2003 | Harima | .......................... | 463/31 |
| 6,632,158 B1 * | 10/2003 | Nashner | .......................... | 482/8 |
| 6,641,482 B2 * | 11/2003 | Masuyama et al. | ............. | 463/44 |
| 6,695,694 B2 * | 2/2004 | Ishikawa et al. | .................. | 463/7 |
| 6,699,188 B2 * | 3/2004 | Wessel | .......................... | 600/300 |
| 6,765,726 B2 * | 7/2004 | French et al. | ................. | 359/630 |
| 6,774,885 B1 * | 8/2004 | Even-Zohar | ................. | 345/156 |
| 6,996,261 B2 * | 2/2006 | deCharms | ..................... | 382/131 |
| 7,018,211 B1 * | 3/2006 | Birkholzer et al. | ........... | 434/257 |
| 7,028,547 B2 * | 4/2006 | Shiratori et al. | ................. | 73/495 |
| 7,062,225 B2 * | 6/2006 | White | ........................ | 455/41.2 |
| 7,331,856 B1 * | 2/2008 | Nakamura et al. | ................ | 463/7 |
| 2001/0031456 A1 * | 10/2001 | Cynaumon et al. | ........... | 434/350 |
| 2001/0041647 A1 * | 11/2001 | Itoh et al. | .......................... | 482/9 |
| 2002/0045519 A1 * | 4/2002 | Watterson et al. | .............. | 482/54 |
| 2002/0055383 A1 * | 5/2002 | Onda et al. | ...................... | 463/36 |

(Continued)

*Primary Examiner* — Loan Thanh
*Assistant Examiner* — Sundhara Ganesan

(57) ABSTRACT

An exercise computer monitors the exercises of a user, especially a child, and provides rewards for exercises done well and regularly, thereby motivating the user. Rewards take the form of video games, cartoons, music, and merchant coupons. The exercise computer also provides encouragement and advice as the user progresses in skill level. Exercises may be prescribed. A record of exercise performance can be produced, to track the user's progress over time. The system and method can readily utilize the current install base of handheld computers and video games pre-existing in the marketplace.

21 Claims, 15 Drawing Sheets

U.S. PATENT DOCUMENTS

| | | | |
|---|---|---|---|
| 2002/0077219 A1* | 6/2002 | Cohen et al. | 482/8 |
| 2002/0103429 A1* | 8/2002 | deCharms | 600/410 |
| 2002/0107433 A1* | 8/2002 | Mault | 600/300 |
| 2002/0109600 A1* | 8/2002 | Mault et al. | 340/573.1 |
| 2002/0128119 A1* | 9/2002 | Arai | 482/8 |
| 2002/0165067 A1* | 11/2002 | Watterson et al. | 482/54 |
| 2003/0050537 A1* | 3/2003 | Wessel | 600/300 |
| 2003/0087220 A1* | 5/2003 | Bessette | 434/247 |
| 2003/0109322 A1* | 6/2003 | Funk et al. | 473/222 |
| 2004/0077462 A1* | 4/2004 | Brown et al. | 482/8 |
| 2004/0229729 A1* | 11/2004 | Albert et al. | 482/8 |
| 2005/0014113 A1* | 1/2005 | Fleck et al. | 434/247 |
| 2005/0035553 A1* | 2/2005 | Lehrer | 273/444 |
| 2005/0113170 A1* | 5/2005 | McHugh | 463/40 |
| 2005/0209049 A1* | 9/2005 | Shields | 482/8 |

* cited by examiner

DEVICE AND METHOD FOR EXERCISE PRESCRIPTION, DETECTION OF SUCCESSFUL PERFORMANCE, REPORTING, AND PROVISION OF REWARD THEREFORE

CROSS REFERENCE TO RELATED APPLICATIONS

This application is a continuation of U.S. patent application Ser. No. 10/901,266, filed Jul. 28, 2004, now U.S. Pat. No. 8,109,858, incorporated herein by reference in its entirety.

FIELD OF THE INVENTION

The present invention relates generally to an exercise device and method for prescribing and measuring the physical activity of individuals, especially children. More particularly, it relates to an exercise device and method for prescribing physical exercises and measuring and evaluating the performance thereof for the purposes of reporting and providing a reward for exercises successfully completed, and driving subsequent exercise prescription.

BACKGROUND OF THE INVENTION

A significant concern of the present day is an upsurge in childhood obesity. Results feared from this situation include an increase in the diabetic population, and the dramatic concern that this generation may be the first to have a shorter expected life span than its progenitor.

Though proper diet will play a role in correcting this situation, physical activity and exercise will be key.

A number of experts identify television viewing, computer games, and browsing the Internet as non-physical activities in which young people are devoting increasing amounts of time, to their detriment. While these activities are not inherently unhealthy, their innate attractiveness results in the large degree by which they supplant more active pass-times, and that displacement seems to be causing harm to children at large.

Video Games to Motivate Exercise

It should be possible to harness the attractiveness of television, video games, and the Internet to motivate people, especially children, to get more exercise. Indeed, numerous products have linked physical activities to popular consumer electronic entertainment devices.

In an attempt to encourage video game players to convert their play time into an exercise session, a variety of video game controllers have been created which require some form of physical exertion to generate the signals needed to control a video game.

For instance, in U.S. Pat. No. 5,645,513, Haydocy et al. teach a stationary bicycle as a controller for a game console. In U.S. Pat. No. 6,183,365, Tonomura et al. and in U.S. Pat. No. 6,669,563, Kitami et al. teach a boxing glove sensor as a controller for a game. Numerous other examples exist of exercise-based video game controllers, including sensors for tracking swinging arms and kicking legs, and exercise on a stepper machine.

Generally, these suffer from one or more of three drawbacks. First, the control is often inelegant and clumsy, for instance, where large body motions are required to trigger events that are usually represented by a rapid series of button presses. In such a case, the play and enjoyment of the game can be seriously disrupted. Second, the exercise-based controller is rarely well integrated into the video game. Functions requiring combinations of buttons on a regular controller may not be accessible on the exercise based controller (e.g. holding both feet off the ground). Third, the effects of exercise may inhibit the playability of a game. Exercise machine noise may drown out crucial audible hints or instructions. Heavy breathing and sweaty hands may compromise attentiveness and reaction time. In general, concurrent exercise is sure to degrade a gaming experience, though concurrent game playing may improve an exercise experience.

Playing to this positive aspect, exercise equipment was designed that incorporates game and simulation elements. Rather than attempting to introduce exercise into pre-existing games, special games were designed where greater exertion on the exercise equipment would produce a greater desirable response in the game. Examples include those systems taught by Hall-Tipping in U.S. Pat. Nos. RE34,728 and 5,362,069, and Dugan in U.S. Pat. No. 5,947,868. This class of systems is ultimately unsatisfying due to their limited repertoire: they come with one or few games or scenic software loads, and rarely, if ever, are more made available. Further, the game industry, like Hollywood, is a hit-driven industry. The likelihood that a specific game will be a hit is low. Limiting adoption of such systems further is the fact that exercise equipment incorporating games and simulation tend to be expensive relative to both ordinary game consoles and standard exercise equipment.

Some compelling games have been designed from the outset to incorporate physical movement, either urgent or sustained, which results in a good physical workout.

DanceDanceRevolution, by Konami Corporation, LTD, of Tokyo, Japan, was initially available only for arcades because of its specialized foot-position-sensitive dance platform. Loud, rhythmic music plays and a scrolling series of arrows indicate upon which positions on the dance platform the player should step for the next beat. At advanced levels, a successful player is receiving a high impact aerobic workout! The game, a rare hit, has become so popular that home versions of the foot-position-sensitive platform are available (such as the RedOctane Dance Pad by RedOctane of Sunnyvale, Calif.) for use with consumer gaming consoles (such as the PlayStation 2 by Sony Computer Entertainment America, Inc. of Foster City, Calif.). Though very successful to date, DanceDanceRevolution has drawbacks: The area where the game can be played is limited to the dance platform (or home version pad), there is a limited repertoire of useful movements, and the single game-driven motivation is to achieve a better score.

In a different direction, U.S. Pat. Nos. 6,213,872 and 6,302,789, both by Harada and Shimizu, teach that the count of a user's steps made by an electronic pedometer can control an animated character, and provide a unit of exchange within a game. Productized by Nintendo of America, Inc. of Redmond, Wash., as "Pokémon Pikachu 2 GS™", the self-contained pedometer and game includes a display screen, clock, control buttons, and an IR communication port. The count is converted to an in-game currency, "Watts," which can be used in four contexts. First, to the animated character, which simulates a pet, Watts can be given as a treat that makes it happy. Second, Watts can be used as a gambling currency in a card game, which pays off in Watts. Third, Watts can be transferred via the IR port from one pedometer to another, like device. Fourth and finally, Watts can be transmitted via the IR port to compatible Nintendo GameBoy® games, specifically Nintendo's games "Pokémon Gold™" and "Pokémon Silver™", wherein the Watts activate a gift to a character in that game.

There is a significant drawback to the Harada and Shimizu pedometer game, however. Their pedometer, as is common, uses a vibration detector to detect steps. According to the "Pokémon Pikachu 2 GS" pedometer instructions, " . . . the number of steps you take each day will be counted . . . " and it " . . . will also count your movements when you run, jump or skip." In fact, it will count just about any motion. The indiscriminate nature of a vibration count opens a source of significant cheating by players: By merely rattling the pedometer in one's hand, "steps" are detected, at far greater speed, and with far less effort, than are archived by actual walking. In one test, five minutes of rattling was approximately equivalent to a day's worth of walking. To the extent that the rewards offered for steps are compelling, the player is motivated to rattle the device and gain the rewards immediately, rather than walk and have them tomorrow.

Rewards and Games

Many game machines offer rewards. Almost all games offer scores. A score is given for certain achievements, and is, to some degree, a function of skill. Your lap time, in a race; ten points each time the ball strikes a mushroom bumper in pinball; thirty points for each pointy-headed alien shot in Space Invaders™ by Taito; are such scores are improved with higher degrees of skill. But scores alone are intangible and usually fleeting rewards.

Redemption games, usually found only in arcades, offer coupons in exchange for high scores. The coupons can be redeemed for broad array of prizes, rewarding skill with real-world treasures. This makes redemption games extremely popular with children and adults.

In Mario Party™ and its sequels, all by Nintendo of America for their Nintendo®64 and GameCube™ consoles, high scores can be redeemed for access to still more games. A predetermined collection of mini-games is present within the Mario Party™ cartridge. However, when first activated, none of the mini-games is available for players to play at will. Only by playing the main game well and successfully earning points can individual mini-games be acquired for on-demand play.

Accelerometers in Games

In U.S. Pat. No. 6,641,482, Masuyama and Suzuki teach using a pair of accelerometers in a handheld game to detect a tilting of the handheld unit, and to use the tilt measurement to affect the motion of characters and objects on the screen. Realized as Kirby Tilt 'n' Tumble™ by Nintendo for their Gameboy® console, the accelerometers detect the pitch and roll orientation of the handheld game console. In response, characters and objects within the game roll or drift about the handheld screen as if they were pinballs, actually under the influence of gravity.

Flash Cartridges for Handheld Games

As memory capacities have grown over the years, the size of computer games has grown, too, though not as quickly. Today, a single flash memory chip contains enough memory storage to hold images of up to many dozens of game cartridges from years past. This, in conjunction with the Internet, has given rise to a great bane of handheld game cartridge manufacturers: Third-party handheld game accessory manufacturers are selling flash memory-based cartridges, which allow illegal copies of game programs extracted from legitimate cartridge ROMs to be easily distributed over the Internet and freely loaded into any number of flash memory cartridges, thereby undermining the market for both new and old games. For example, a flash cartridge product called EZ-Flash Advance advertised for the Nintendo GameBoy® on a web site called www.gameboy-advance.net by an third-party manufacturer (that has gone to some length to obscure its identity) includes 256 MB of flash memory in a cartridge adapted to work in the Nintendo GameBoy Advance™ handheld game system, and a USB cable that communicates between the GameBoy Advance™ and a PC. With the cable connected, the PC is able to upload the ROMs of legitimate cartridges plugged into the GameBoy® to a file, or download a file into the EZ-Flash cartridge. Both activities infringe the intellectual property rights of the ROM copyright holder. The pirate files are easily uploaded to the web (or emailed) and the web site promotes links to peer-to-peer file sharing groups to make finding pirated files easy, adversities faced by the music industry since the advent of MP3 players.

Though flash-based cartridges promote illegal trafficking in pirated ROM files, their allure is sure. The price for a 256 MB flash cartridge is roughly three times the price for a like-sized, but legal, flash disk with USB interface for a PC. That overage is roughly the cost of three or four new, legitimate, game cartridges. Besides providing access to pirated games, the flash cartridges also provide a high degree of convenience. The ability to carry a single cartridge with an entire library of games is a distinct advantage over the present requirement of toting many little cartridges, which are awkward and easily dropped or misplaced.

A significant disadvantage of present day ROM-based cartridges, one that is exploited by flash-based cartridge pirates, is that a ROM image from a single game cartridge is usable in every compatible handheld game system. An analogous disadvantage is present with MP3 music files, and the MPEG files that comprise video programming on DVDs.

Summary of Needs Unsatisfied by Prior Art

These prior electronic game and exercise technologies have failed to meet a number of needs.

There remains a need for a system capable of recognizing distinct, specific exercises, so that a well-balanced regimen of exercise can be prescribed and/or monitored.

There remains a similar need for a system able to measure skill level in performance of an exercise. Not merely a need for tracking a count of repetitions, but for a system able to discern between an exercise done skillfully, and an exercise done improperly.

When an exercise is recognized by the system as being performed improperly, there is a need for the system to provide corrective advice.

When an exercise is performed, correctly or not, there is a need for the system to deliver appropriate encouragement to the user.

The need exists for a system that tracks the progress of the user as he grows in skill, so that the system can prescribe new exercises appropriate to the user's advance.

There is the need for a system to prescribe exercises appropriate to the achievement of a health goal, but without exceeding the present capabilities of the user.

An audio interface is needed that will allow a user, while performing exercises, to receive instructions, encouragement, criticism, and advice, pertinent to the exercise.

A supreme need is for a way to reward a user, especially a child, for undertaking, advancing, and maintaining a level of healthful exercise.

There is a need for a way to provide as a reward, when appropriate, games or other entertainment built into an exercise promoting system.

There is a similar need for providing games or other entertainment that come to the exercise promoting system from an external source, so that the pool of rewards is continually updateable.

As already recognized from redemption games, the availability of physical prizes as a reward for achievement is a powerful motivation. There is an unmet need for harnessing this motivation with respect to exercise.

The need persists for a way of moderating access to the Internet, computer games, and television, so that these sedentary activities are not allowed to displace too much healthful, active play.

Given the motivations that a reward structure will engender, a system is needed that will resist efforts at cheating.

A system is needed that will prevent or minimize the inappropriate re-use of rewards. A one-time reward, though delivered electronically, should not be duplicated or reusable.

A further need exists for preventing or minimizing the inappropriate re-distribution or sharing of rewards. That is, a reward provided to one user should not be accessible to another user.

There is also the need, in cases where the user is a child, for notifying the parents of the child's performance in the exercise program. This is to provide both satisfaction to the parents that the child's activities include healthful exercise, and enough information for them to intervene and correct the situation if the child's activities (including attempted cheating) fall short of expectations.

The present invention satisfies these and other needs and provides further related advantages.

OBJECTS AND SUMMARY OF THE INVENTION

The object of the present invention is to prescribe and measure the physical activity of individuals, especially children.

It is an object of this invention to prescribing physical exercises, measuring and evaluating the performance thereof, and to provide a reward for exercises successfully completed.

It is a further object of this invention, having measured and evaluated performance of prescribed exercises, to provide subsequent exercise prescription.

It is an object of this invention to recognize and evaluate the performance of any exercise of a predetermined collection of exercises, without the requirement for a prescription or user-provided identification of the exercise.

An object of the present invention is to promote a well-balanced regimen of exercises by prescription and/or monitoring, and subsequent provision of feedback to the user.

Measuring the skill level in performance of an exercise is a further object of the present invention: Beyond merely tracking a count of repetitions, it is an object to be able to discern between an exercise done skillfully, and an exercise done improperly.

It is an object of the present invention, when an exercise is recognized as being performed improperly, to provide corrective advice.

A converse object is, when an exercise is performed, correctly or not, to deliver appropriate encouragement to the user.

An additional object of the invention is to track the progress of a user as he grows in skill, and prescribe new exercises appropriate to the user's advance.

It is an object of the invention to prescribe exercises appropriate to the achievement of a health goal, but without exceeding the present capabilities of the user.

A further object of the invention to provide an audio interface that allows a user, while performing exercises, to receive instructions, encouragement, criticism, and advice, pertinent to the exercise.

A key object of the invention is to reward a user for undertaking, advancing, and maintaining a level of healthful exercise.

It is an object of the invention to provide built-in games, or other entertainment, as a reward to promote exercise.

It is an object of the present invention to promote exercise by providing rewards from an external source, so that the pool of rewards is enormous, and/or continually updateable.

A further object of the invention is to make available physical prizes as a reward for achievement in exercise, by providing electronic coupons, which can be redeemed external to the system.

It is an object of the present invention to moderate access to the Internet, computer games, and/or television, so that these sedentary activities are not allowed to displace too much healthful, active play.

It is an object of the present invention to resist efforts at cheating.

A further object is to prevent the inappropriate re-use of rewards, such that a reward delivered electronically and intended as being single use, is not reusable.

Another object of the present invention is to prevent inappropriate re-distribution or sharing of rewards, so that a reward provided to one user is not accessible to another user.

An object of the present invention is, in cases where the user is a child, to notifying the parents of the child's performance in the exercise program, to provide both satisfaction to the parents that the child's activities include healthful exercise, and enough information for them to intervene and correct the situation if the child's activities (including attempted cheating) fall short of expectations.

These and other features and advantages of the invention will be more readily apparent upon reading the following description of a preferred exemplified embodiment of the invention and upon reference to the accompanying drawings.

BRIEF DESCRIPTION OF THE DRAWINGS

The aspects of the present invention will be apparent upon consideration of the following detailed description taken in conjunction with the accompanying drawings, in which like referenced characters refer to like parts throughout, and in which.

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE INVENTION

Figure 1:
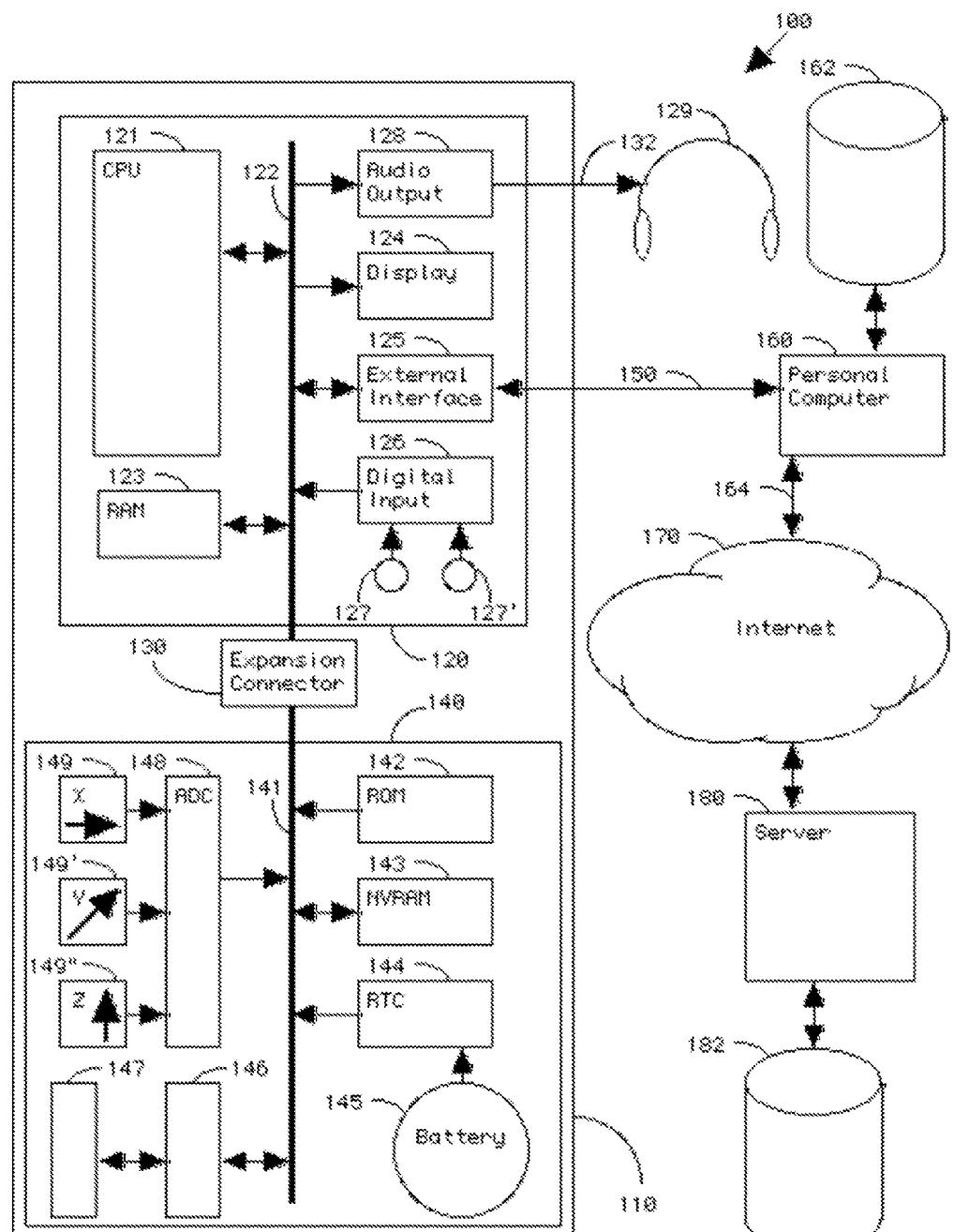
FIG. 1 is a detailed block diagram of an exercise computer having accelerometers for detecting the motions of exercise.

The preferred embodiment of this invention is wearable exercise computer 100, shown in FIG. 1. Wearable exercise computer 100 is comprised of handheld computer 120, a carrying case 110 or other holder, clip, or pocket adapted to hold the handheld computer 120 close to the wearer's body and not loose.

Handheld computer 120 contains CPU 121, and address/data bus 122, RAM 123, a display 124 with driver circuitry and display memory (not shown), an external communications interface 125, and digital input interface 126 for reading one or more buttons 127 and 127'. An audio output circuit 128 preferably drives headphones 129 via headset cable 132, though a wireless connection or an internal speaker may be used instead. Handheld computer 120 also includes a power supply, preferably in the form of rechargeable batteries (not shown).

Such handheld computers and variations on the theme are well known. Specific examples include the "Personal Digital Assistants" (PDAs) manufactured by palmOne, Inc. of Milpitas, Calif. and the GameBoy® line of handheld game consoles by Nintendo of America Inc. of Redmond, Wash.

Peripheral devices not commonly found in handheld computer 120 are supplied in cartridge 140. Preferably, cartridge 140 inserts into and connects to handheld computer 120 through expansion connector 130. Expansion connector 130 allows the address/data bus 141 of cartridge 140 to connect with address/data bus 122 of computer 120. Cartridge 140 includes ROM 142 for containing software implementing the present invention, preferably some form of non-volatile RAM 143 (e.g. EEPROM, or battery-backed SRAM), a real-time clock 144 powered by battery 145, a large non-volatile memory 147, such as a flash memory, and a bus interface 146 to perform bank addressing, if needed. Each of these elements is well known and has been provided many times for portable computer devices, such as the Nintendo GameBoy®.

Also in the cartridge, though not frequently provided in prior art cartridges, is a plurality, preferably a trio, of accelerometers 149, 149', and 149", each preferably addressing an orthogonal axis, preferably axes X, Y, and Z (as defined below) when the cartridge 140 is inserted into the computer 120, placed in carrying case 110, and worn by the user. Accelerometers 149, 149', and 149" read at least +/−1 G, and preferably about double that (+/−2 G). Their electrical output is digitized and made available to CPU 121 by analog-to-digital converter (ADC) 148. The accelerometer signals are preferably conditioned by analog circuitry (not shown) before reaching ADC 148 so that the full range of likely readings is fitted to the range of ADC 148, and filtered so that the Nyquist criterion is met. Signal conditioning of accelerometers for ADC interface is well known in the art. Most meaningful accelerometer signals during exercise are expected to fall below 10 Hz. However, some meaningful transient accelerations may be useful for detecting specific exercises of interest, in which case, design and testing at a somewhat higher bandwidth may be necessary. In particular, high-impact exercises may generate transients having higher frequency components, and correct detection of such components may be necessary to recognizing the correct performance of such an exercise.

Alternatively, transient sensor phenomena may be captured with interrupt driven threshold detection triggered circuitry (not shown), or peak value detectors (not shown), or other methods available to those skilled in the art. Such methods allow relatively infrequent processor attention, even for capturing very short-lived sensor events (e.g. impacts, inflections, peaks, zero-crossings, etc.) that may be selected as identifying characteristics of an exercise.

While it is preferable to retain the economy of adapting a pre-existing handheld computer 120 to the purposes of the present invention, by providing the uncommon elements in the form of cartridge 140, an alternative embodiment would provide all of the functional elements in one dedicated unit. Further, appropriate adaptations made to the case of handheld computer 120 would incorporate the function of carrying case 110, so that a completely integrated unit is possible.

In still another alternative embodiment, the some or all of sensors elements 149, 149', and 149" of cartridge 140 can be physically remote from the body of wearable exercise computer 100, attached by a cable or wireless link.

For some embodiments of this invention, a capability for connection to the Internet 170 is needed. If handheld computer 120 is not otherwise ready for network connection, e.g. through a built-in modem or wireless communications (not shown), external interface 125 can connect via adapter 150 to personal computer 160, having connection 164 to the Internet 170. Common implementations of external interface 125 include serial connections of various types, such as variations on RS-232, and USB (other alternative implementation are described below). Whether the implementation of external interface 125 is directly compatible with personal computer 160 will determine whether connection 150 is implemented as merely a cable, or as a signal and/or protocol converting adapter. In the case of the Palm products, most earlier models have simple RS-232 serial ports and only require a correctly wired cable. Later Palm models produce USB signals. The link port on Nintendo's GameBoy® is a clocked serial device operating at about 8.3 kilobaud, and so requires an adapter for connection to common personal computer interfaces.

In an alternative embodiment, external interface 125 may be located in cartridge 140 and connected to bus 141.

Personal computer 160 may have local storage disk 162, and data may be transferred from wearable exercise computer 100 via connection 150 and stored on disk 162. The well-known and highly touted "conduits" associated with Palm applications exemplify this function.

Through the Internet 170, a user can interact with a web site or other service provided by server 180. Just as data can be moved from the wearable exercise computer 100 to the storage 162 in personal computer 160, so too can data be transferred to storage 182 of server 180. Conversely, data from server 180 can be moved either to personal computer 160, or through computer 160 and connection 150 to wearable exercise computer 100, and thereby to one of the writeable memories 143, 147 in cartridge 140.

While the connection between wearable exercise computer 100 and server 180 is depicted as being routed through personal computer 160, that is not strictly required. For example, if external interface 125 comprises a wireless communications capability, then connection 150 is a wireless link, and personal computer 160 would be replaced by a wireless router. Alternatively, external interface 125 can comprise a modem and the connection to server 180 may be achieved via a telephone connection, which may or may not involve Internet 170, and may or may not be wireless. Such modes of connecting portable devices to remote servers is well known to those skilled in the art.

Preferably, to minimize the opportunity for cheating, information from server 180 is provided to accurately set RTC 144.

Since such devices as handheld computer 120 exist in the consumer market in large numbers and the design of cartridges and software for them is well known. For some devices, this is because the manufacturer has published specifications. In other case, the design is well known because the results of reverse-engineering efforts have been published. For some common handheld computers, the legal production of operable software and cartridges requires licenses to copyrighted or otherwise protected codes from the manufacturer.

Figure 2:
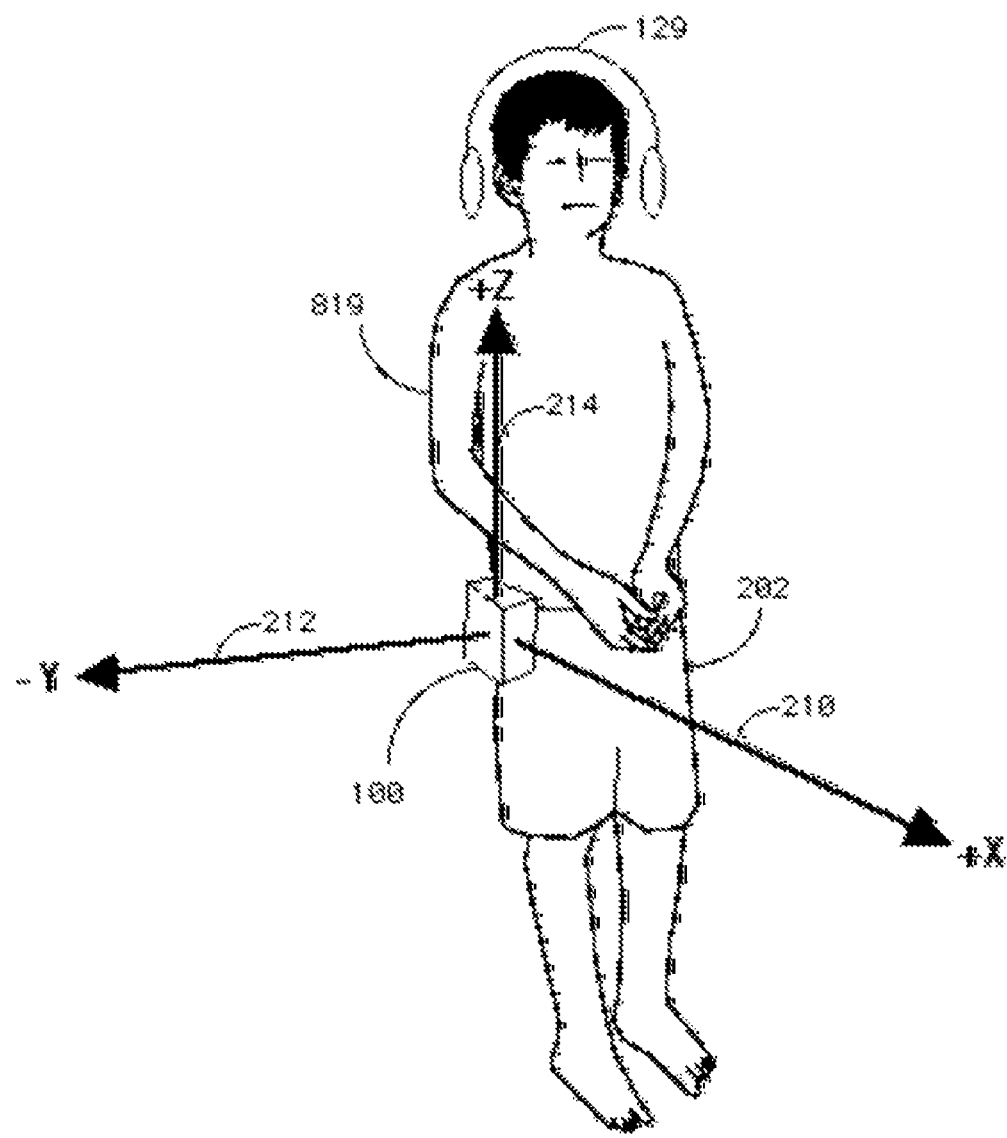
FIG. 2 shows a preferred position of the handheld computer while in use, with the accelerometer axis orientation reference used herein.

FIG. 2 shows a user 819 at rest, with wearable exercise computer 100 preferably attached to his pants 202 via his belt or a pocket (not shown), so as to remain in approximate and consistent alignment with his hips. Alternative embodiments may rely on consistent alignment with other body parts. User 819 is wearing headset 129 connected to wearable exercise computer 100 by headset cable 132 (not seen in FIG. 2). In an alternative embodiment, the connection to headset 129 may be wireless. For the purposes of this document, the orthogonal axis vectors 210, 212, and 214 represent the +X, −Y, and +Z directions respectively, forming a right-handed coordinate frame where positive Z is up, positive X is forward, and positive Y is to the user's left. In the orientation shown in FIG. 2, Earth's gravity provides a constant 1.0 G in the negative Z direction.

For this coordinate system, positive pitch would measure the angle off horizontal by which positive X points downward, to a maximum of +90 degrees. Negative pitch points the X-axis upward, to a limit of −90 degrees (straight up). For this definition, pitch can be calculated by the formula PITCH=ARCSIN(x), where x is the reading of accelerometer 149, limited to the closed interval [−1, 1].

Roll is measured as rotation about the X-axis, with positive roll resulting from the positive Y-axis being swept toward the positive Z-axis. For this definition, roll can be calculated by the common math function ATAN2(−z, −y). The well-known ATAN2 function is similar to the trigonometric function ARCTANGENT, except that it takes the opposite & adjacent parameters separately, rather than as a ratio. Thus, ATAN2 is able to identify angles in the semi-closed range [+180, −180) because it can identify combinations in all four quadrants, whereas the ARCTANGENT can only return angles in the closed range [−90,+90] because its single parameter, the ratio of opposite to adjacent, cannot distinguish between quadrant I and quadrant III, nor between quadrant II and quadrant IV.

Yaw would be measured as a rotation about the Z-axis, positive in the direction of X sweeping toward the positive Y-axis. However, yaw is not detectable purely from the gravitational field, since the G field is essentially symmetrical about the vertical Z-axis. If a particular class of exercises (e.g. dance moves, such as a pirouette) required accurate measurement of motion about the yaw axis, it would be appropriate to add additional sensors to detect yaw.

One option would be to introduce a compass sensor (not shown) that could detect orientation of user 819 with respect to the Earth's magnetic field (not shown). Such a sensor would be connected to bus 141 though additional channels of ADC 148, or by other well known methods. An example of an appropriate compass sensor is the HMC6352 2-Axis Digital Integrated Compass by Honeywell International Inc. of Morristown, N.J. This circuit combines a two-axis magneto-resistive magnetic field sensor with the required analog and digital support circuits for heading computation at up to 20 Hz. By differentiating the heading signal, a yaw rate may be obtained. This is preferable for exercises that are not concerned with the initial orientation, but only require a relative measurement of rotations about the Z-axis. As will be seen below, not only direct sensor signals, but also functions of the original signals can be used to detect performance of exercises. For certain exercises, for instance Tai Chi, an absolute facing (e.g. "start by facing east") is preferred.

Another technique would be to use an angular rate sensor, such as the ADXRS300 by Analog Devices of Norwood, Mass. The angular rate sensor operates as a gyroscope to detect the yaw rate.

In certain circumstances, reasons exist for configurations having additional accelerometers. For instance, an additional pair of accelerometers on the non-ordinal XY and XZ axes would allow a more precise measurement of pitch as the X-axis approaches the vertical, since near the vertical, a small change in x-axis accelerometer 149 reading will represent a larger angular variation than the same small change when the X-axis is near the horizontal. For instance, if accelerometer 149 has a total range of +/−2 G, and ADC 148 has a 10-bit resolution, then an error of a single bit when reading near 1 G (i.e., near vertical) produces an error of 5 degrees, while when near the horizontal, the same single bit represents 0.2 degrees of error in pitch. The additional accelerometer readings can be used, with more complex formulae, to measure pitch more accurately. Such techniques, and other, for improving resolution are well known and within ordinary skill in the art, but for most exercises, the extra accuracy is unnecessary.

Still another kind of sensor that may be incorporated into cartridge 140 is a Global Positioning System (GPS) receiver (not shown). Compact GPS receivers are well known for their ability to determine their location, altitude, speed, and direction of movement by analyzing the signals received from a constellation of navigational satellites. Such receivers are commonly provided with a geographic database to present a user with a map of his surroundings. In this invention, the parameters of location, altitude, speed, and direction of movement can be added to (or in some cases replace) the information provided by other sensors to distinguish between, for instance, riding in a car and riding on a bicycle, or between running on level ground and running up a hill.

Within the scope of the present invention is the use of fluxgates, GPS, or other varieties of sensors to improve the range of exercises that can be detected or to improve the discrimination and reliability of detection. It is also considered within the scope of this invention that such sensor technologies may be able to supplant the use of accelerometers 149, 149', and 149" in the preferred embodiment. For the purposes of further discussion, the preferred embodiment of accelerometers is presumed.

Further, those skilled in the art will recognize that sensors such as 149, 149', and 149" can be remoted from CPU 121 by a wireless interface, so that only the sensors, a transmitter (not shown), and a power supply are worn by user 819. Signals from the sensors would be detected by a receiver and made available to CPU 121.

Monitoring Exercise Performance

Figure 3:
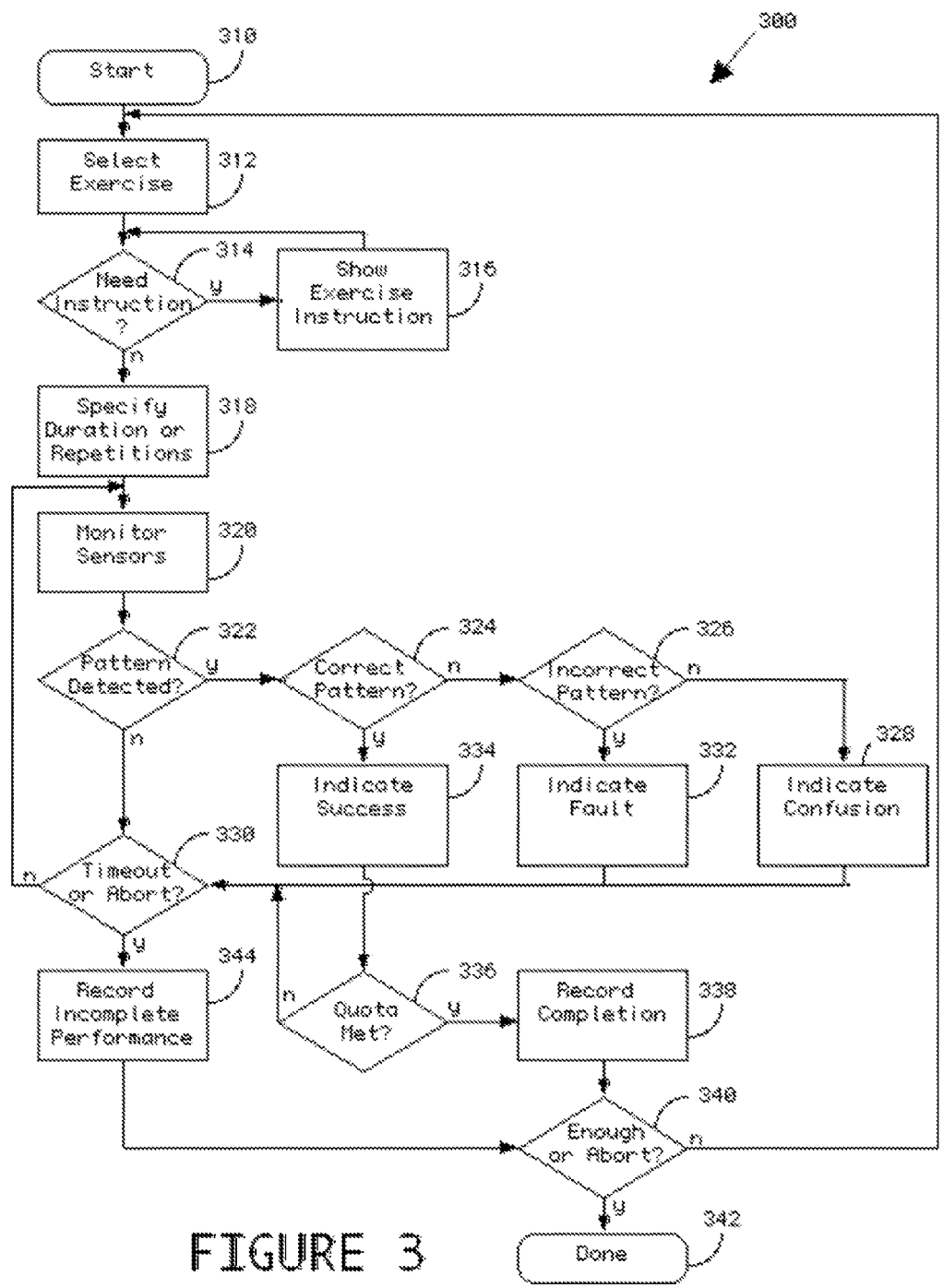
FIG. 3 shows a flowchart for a procedure to prescribe, detect, and reward the performance of an exercise.

Referring to FIG. 3, the preferred embodiment of a process for a monitored exercise session 300 is shown.

In step 310, the exercise session initializes. If prior monitored exercise sessions 300 have run for the current user, the data collected or summarized from such sessions should be available for local access, preferably from NVRAM 143 or flash memory 147. The preferred nature of exercise history data 1000 is described below in conjunction with FIG. 10. If no previously collected data 1000 is available (as would be the case when process 300 is first run), then the appropriate storage should be initialized from templates stored as part of the program in ROM 142. The specific templates used to initialize individual exercise records 1010 are those predetermined to be appropriate for a first-time user. Generally, these will be the simpler exercises, and those for which initial, modest goals can be set (e.g. chin-ups, but not one-armed chin-ups).

In step 312, the next exercise is selected. The selection is preferably performed automatically, based on an analysis of the exercise history data 1000. An example algorithm would be to select the least-recently-performed exercise from among the records 1010.

User 819 may have the opportunity in step 312 to reject a selected exercise, in which case another selection is made. This is a valuable option, for instance, if the recommended exercise is a five-mile run, but it happens to be raining. In combination with the least-recent exercise selection mentioned above, it ensures that this exercise will be recommended again during the next monitored exercise session 300.

Alternatively, step 312 may present to user 819 a list (not shown) of appropriate exercises from which to select the one to perform next.

Other alternative mechanisms can be used in step 312 to select an exercise, for instance the selection of appropriate exercises could be random.

The selection algorithm used in step 312 can be further augmented by introducing new exercises recognizable in step 320, below, but for which no exercise record 1010 has been yet established. For instance, certain exercises may be introduced into the repertoire only after a prerequisite exercise has been mastered. Further, if according to exercise history data 1000 a user 819 seems to be having difficulty with an exercise, then it may be replaced in the repertoire by a remedial exercise until such time as user 819 has demonstrated a suitable degree of mastery, strength, or stamina.

Whether an exercise is actually added to or removed from exercise history data 1000 is an implementation detail. In some implementations, NVRAM 143 may be limited, and the number of records 1010 stored there may need to be minimized for economy. However, if this is not the case, and records for all exercises usable in step 320 are to be kept, then a flag (not shown) of "active" exercises is preferably included in each of records 1010.

Still another alternative, which bypasses step 312 altogether, would be to allow user 819 to simply proceed with his own choice of exercise, and leave it up to step 320 to recognize exercises as they are performed. This is feasible if the recognition abilities of step 320 are sufficient to either effectively distinguish among specific exercises, or effectively distinguish among populations of exercises having significantly similar benefits and/or values (described below). In such a case, steps 312, 314, 316, and 318 are bypassed (this bypass from step 310 to step 320 is not shown).

In step 314, instructions are offered for performing an exercise selected.

Figure 4:
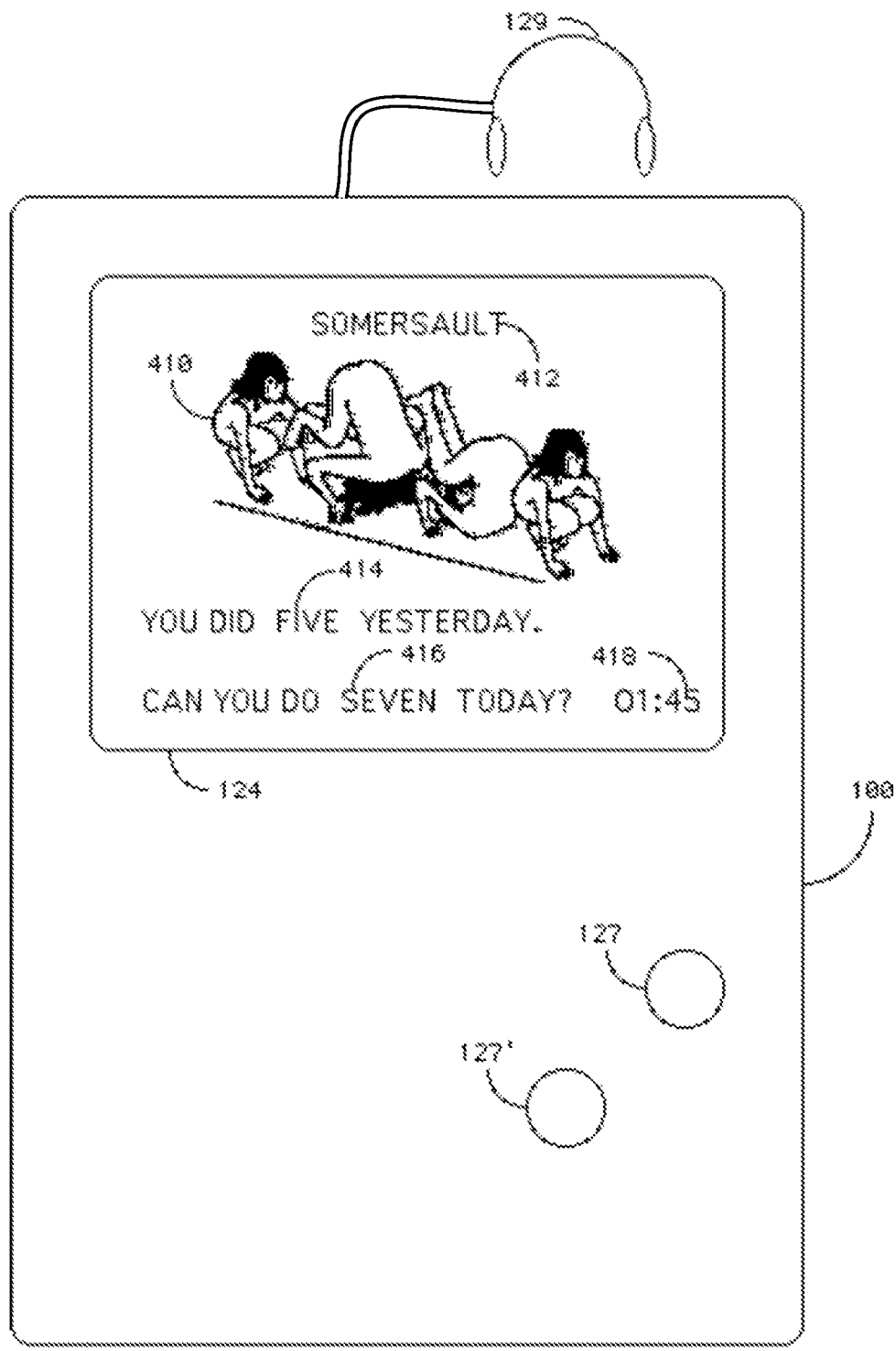
FIG. 4 shows an exemplary display screen for prescribing an exercise (a somersault)

If accepted by user 819, the exercise instructions are shown to the user 819 in step 316. Such instruction may comprise any combination of simple descriptive text, an illustration, instructive audio, or an animation. An example of instructions is shown in FIG. 4, wherein the display 124 of wearable exercise computer 100 is showing an animation 410 illustrating the exercise named by legend 412.

It may be the case that upon seeing the instructions, user 819 would rather reject the selected exercise and return to selection step 312 (this optional choice is not shown), for instance by pressing button 127'.

In step 318, a duration for the selected exercise, a number of repetitions, or preferably both, are presented to the user as a goal for the immediate. Referring again to FIG. 4, the target duration 418 is shown, along with target repetition count 416. When both duration and repetitions are presented, they may come in this form. Alternatively, such challenges as "How fast can you do seven somersaults?" or "How many somersaults can you do in two minutes?" may be issued. If this is not the user's first attempt at the selected exercise, the repetitions 1015 from the most recent historic exercise record 1010' for the same exercise can be presented as a reminder 414. An analogous reminder may be constructed from actual elapsed time 1017 from the same historic exercise record 1010'. Similarly, best-performance reminders may be generated from records 1010' for the same exercise 1011 having the highest repetitions 1015 or the best actual elapsed time 1017.

The challenges of step 318 are preferably recorded in exercise record 1010. The exercise selected is recorded in exercise ID 1011. The session number 1012 records, for this exercise session, a sequence number or, in the alternative, the date and time as read from RTC 144. A skill expected 1014 is computed by trending skill grades 1013 from prior exercise records 1010' having the same exercise ID 1011. A requested repetitions 1016 and target time 1018 is similarly computed from historic trends of actual repetitions 1015 and elapsed time 1017, respectively.

The computation of trends for skill expected 1014, requested repetitions 1016, and target time 1018 should consider both recent performances and built-in improvement targets. For expected skill 1014, the built-in improvement target will produce a slow growth, as a whole point of improvement may represent a transition between skill levels in an exercise (e.g. the difference between learning a cartwheel, and having mastered it). However, if user 819 repeatedly exhibits a high degree of skill, the trend of recent performances will reflect that high degree of skill, so the slow growth target will not inhibit fast learners. The built-in improvement for requested repetitions 1016 will be for more repetitions, but an increment of 1 or 2 will likely be sufficient over the recent trend. Penetration into the range of the built-in improvement is a success, and meeting or exceeding the built-in improvement is a great success. Depending on the exercise, the built-in improvement may represent a shorter or longer target time. If the exercise is "run around the block" then the built-in improvement could be to shave five seconds off the target time. If the exercise is "stand on your head" the built-in improvement could be to add ten seconds to the target time.

Some exercises or challenges may not warrant a repetition count, as in "How long can you stand on your head?" Similarly, some exercises may not warrant a duration, as in "Do 100 jumping jacks." However, a time limit is usually appropriate and is valuable for the timeout of step 330, discussed below.

Occasionally, neither a repetition count nor duration is specifically identified in a challenge, as in "Stand on your head?" The presence of an ultimate time limit is appropriate, even if unstated for an exercise, as an open-ended activity might otherwise admit the possibility of an infinite loop in process 300.

In step 320, sensor 149 and the others are monitored through ADC 148 by CPU 121 for patterns representing the exercise previously selected.

A specific algorithm suitable for the monitoring of step 320 is described below in conjunctions with FIGS. 5, 6, 7, and 8, though many other suitable algorithms may be used or developed. The key properties of the monitoring algorithm are the following:

The sensors 149, 149', and 149" are read through ADC 148 at frequency sufficient assure the capture of sensor events necessary for the correct detection of an exercise's performance. For most exercises, reading the sensors at 20-30 Hz will be more than adequate, yet not too burdensome. As discussed above, alternative techniques may be used for reducing the processor's sampling burden, or for capturing faster transient events if necessary for detecting the performance of desired exercises.

Each sensor reading is analyzed in the context of the selected exercise from step 312. If no exercise was selected because step 312 was skipped, then the context for analysis is all exercises currently active (as described above).

Further, with respect to any single exercise, the context may include more than one version of the exercise. Analysis proceeds with each version of each exercise contained in the context.

For instance, a cartwheel may correctly begin to the exerciser's right, or to their left. Unless a more specific version of the exercise were specified, correct performance of either version would be equally satisfying.

Additionally, various versions of an exercise may represent an "incorrect" performances, i.e. a cartwheel wherein the performer does not achieve full leg extension while inverted. The value of explicitly detecting a specific incorrect performance of an exercise is that specific remedial instructions can be provided to user 819, as discussed below in conjunction with step 332.

In some embodiments, credit may be given for the performance of incorrect versions of an exercise. This is particularly valuable when ones ability to perform an exercise (e.g. a cartwheel) is acquired in stages. Each of the early stages would be represented by an "incorrect" version of the exercise, whereas the correct performance version would represent the complete acquisition skill in the exercise.

In a slightly different way, a plurality of versions may embody variations in skill level, as in the difference between an easier two-handed chin-up and a more difficult one-handed chin-up. When the analysis of step 320 can distinguish between performances of two such exercises, it is an implementation decision as to how the two are related. If a two-handed chin up were selected, a one-handed chin-up may be considered as a successful completion with optional consideration given to the higher skill level. However, if a one-handed chin-up were selected, the detection of a two-handed chin-up would be considered as an incorrect performance of the selected exercise.

Each variation of an exercise is associated with a skill grade. Preferably, skill grades are numerical to allow the meaningful averaging of skill grades over multiple repetitions, and the trending of skill grades over multiple sessions.

Additional versions of an exercise are discussed below in conjunction with FIG. 5, for the purposes of accounting for execution speed and user body size.

Further, each sensor reading is analyzed in the context established by recent historic sensor readings, which may represent progress within the performance of the exercise, or may merely represent an unassociated pattern of readings as user 819 prepares to begin.

Finally, as the analysis of step 320 proceeds with each reading, a subset of exercises from the established context will be identified as "not begun", "running", or "completed".

In step 322, the analysis from step 320 is tested to see if a candidate exercise from the context has occurred, that is, analysis has determined that one or more exercises is "completed".

Step 324 evaluates whether one of the exercise patterns the analysis of step 320 determined to have been completed represents a correctly completed exercise (as opposed to an "incorrect" version). In step 324, priority is given to exercise versions having a higher skill grade. Thus, for example, if the user's performance is detected as fitting a profile of both a one-armed pull-up and a two-armed pull-up, credit is given for the one-armed version.

If the evaluation in step 324 determines that no exercise has been performed correctly, then step 326 performs a similar test for versions representing incorrect performances of exercises within the context. If a single incorrect performance has been detected, then in step 332 the incorrect performance is indicated to the user. Preferably, the indication is an audible "oops" tone or instructive message (e.g., "Straighten your back!") delivered via audio output 128 and preferably through headset 129. Alternatively, the same progression to step 332 would occur if a plurality of incorrect performances has been detected, but all can share a common instructive message or tone.

If the incorrect pattern evaluation in step 326 cannot identify a particular fault for step 332, then in step 328 an indication is given that an incorrect performance has occurred, as with the audible "oops" tone, but the instructive message, if delivered, is of a less specific nature (i.e., "You can do better!").

If the evaluation in step 324 identifies a correctly performed exercise, in step 334 that success is acknowledged and recorded. Such acknowledgement preferably includes incrementing a repetitions counter (not shown) on display 124, and providing an audible "success" tone or message (e.g., "Good!") via audio output 128.

The success is also recorded in exercise record 1010 by incrementing repetition count 1015. The skill grade associated with the performance is added into skill grade 1013, when the user is done with the selected exercise, this sum will be divided by the repetition count to provide an average skill grade 1013. Alternatively, at each pass through success step 334, a delta skill grade can be computed and added into skill grade 1013, by the formula (1/repetition count)*(current skill grade—previous skill grade) where repetition count is the value in repetitions 1015 after having been incremented for this repetition, and previous skill grade is the value of skill grade 1013 before this repetition, and current skill grade is a value assigned to the version of the exercise pattern detected.

Alternatively, incorrect performances from steps 332 alone, or both steps 332 and 328 can be treated as repetitions for the purpose of either or both the repetition count 1015 and the skill grade 1013. In such a case, the value of current skill grade is determined as the minimum skill grade of all the incorrect performances detected. Another alternative would be to average the skill grade of all the incorrect performances detected. Still another alternative would be to assign an incorrect performance a skill grade of zero (requiring that superior skill grades are represented by higher numbers).

In step 336, if a specific number of repetitions was specified in step 318, the determination is made as to whether that number of repetitions has been reached. If not, the process continues at step 330. Alternatively, in step 336, if the specific number of repetitions is not met, a message indicating the number completed (e.g., "That's five."), or offering encouragement (e.g., "Just two to go!") can be provided.

Step 330 follows any indication of success or fault from steps 336, 332, and 328, provided the repetitions quota has not been met at step 336.

However, if the quota has been met, then in step 338 a recording of that fact is made, preferably in exercise record 1010. Preferably, an "all done" tone or message is provided via audio output 128 and process 300 continues at step 340. Alternatively, sensor monitoring can continue (not shown) and the user's additional performance will be measured and recorded. With this alternative, step 336 can offer additional messages of encouragement (e.g., "That's twenty-three! How do you do it?")

In step 330, a test is made to detect whether the amount of time allocated to the exercise in 318 has expired, or if user 819 has manually aborted the current exercise, by pressing button 127 as directed on screen 124. If not, then the monitoring of the sensors continues at step 320.

In step 330, for some exercises (e.g., "run around the block") the manual abort may be used as an "all done" signal, to indicate the completion of the task.

Exercises that use an "all done" signal to indicate completion, introduce the opportunity for cheating by user 819. If user 819 prematurely presses the "all done" button while performing the exercise "run around the block", this may be detected as "probably false" if the repetition count (which should correspond to steps taken to circumnavigate the block) significantly departed from previously observed measurements. Such "probably false" indicators may be recorded and accumulated to determine if a user 819 is trying to cheat the system to inappropriately gain rewards, discussed in conjunction with FIG. 9. In such a case, credit for the exercise or improvement may be withheld, either with or preferably without explicit notice to the user. The disadvantage of immediate, explicit notice of cheating, is that such feedback may help the user learn the difference between failed methods of cheating, and successful methods of cheating, with the result that he becomes a learned, successful cheater.

If a timeout or abort has been detected in step 330, then, in step 344, an incomplete performance is recorded, preferably in exercise record 1010. In the alternative embodiment discussed above, however, where the quota has already been met or exceeded, then the performance record 1010 is not overwritten—the record of both the success and the additional performance is allowed to stand. Only the elapsed time 1017 (whether from timeout or abort) is recorded in such a case.

In an alternative embodiment of step 344, if the repetition count is zero or another value representative of less than, for example, 20% of the exertion requested in step 318, then the incomplete performance is not recorded.

In another embodiment, the fraction of the exertion requested in step 318 that must be completed for an incomplete performance record to be made is dependent on the exercise requested and the skill expected in that exercise. For instance, if a previous record 1010 exists for which the currently selected exercise matches requested exercise 1011, and record 1010 shows expected skill 1014 representative of competency (i.e. user 819 has previously shown some competence in this exercise), then a substantial fraction, e.g. >50%, of the repetitions requested in step 318 would be necessary. If however, no prior record 1010 exists for the currently selected exercise, then for easy exercises (e.g. jumping-jacks) a relatively large fraction of the initially recommended repetition count would be required, but for a harder exercise (e.g. cartwheels) a lesser fraction would be needed to count as an earnest attempt and thus warrant recording the incomplete performance.

Ideally, the repetition count and duration are not intended as hard limits. If user 819 is performing excess repetitions of the selected exercise, or meeting a challenge for extended time (i.e. standing on his head for more than the requested 30 seconds), his activity should not be interrupted, but rather the extra performance noted in exercise history record 1010.

If extra duration is considered a desirable over-achievement for a selected exercise, then step 330 will still indicate the target time, but rather than terminating the session by branching to step 344, it will only terminate upon an abort by user 819. In such a case, a maximum timeout, perhaps of an hour longer than previous performances, will still terminate the loop. This would be suitable for distance running.

Alternatively, detection of static position for a minute or so can trigger a timeout. This would abort an exercise, if for instance, wearable exercise computer 100 is detached from user 819 and put away.

In another alternative, a similar automatic abort would occur if an exercise pattern corresponding to the movements of a "cool down" were included as a special exercise version. Detection of performance of this version would increment a separate "end of exercise" count (not shown), which upon exceeding a predetermined threshold value would initiate an abort in step 330. The threshold value could correspond to, perhaps, 30 seconds of "cool down".

In step 340, if an exercise record 1010 has been created for the selected exercise, a copy of the current value of RTC 144 is recorded in a storage location in NVRAM 143 representative of Date of Last Exercise (not shown). Further, copy of the Next Exercise Session Number (not shown, but discussed below) from NVRAM 143 is recorded in session number 1012. Alternatively, a copy of the current value of the RTC 144 could be recorded in record 1010 as a performance date (not shown).

Once the exercise has terminated through either step 338 or step 344, a determination is made in step 340 as to whether enough exercise has been done in this session. For the most part, step 340 performs an automatic evaluation, seeking to achieve a certain amount of exercise per daily session, and achieving a certain level of exertion on the part of user 819. For instance, a total of thirty minutes of exercise by user 819, at or above his recent levels of performance would be sufficient. Optionally, if user 819 is performing below his recent levels of performance, some extra time may be added.

Regardless of the automatic determination in step 340, user 819 would have the option of continuing or ending the current session by over-riding the automatic decision. For instance, the user may want an extra five minutes of an additional exercise, and would therefor continue the session. Or, the user may have gotten a late start, needs to abbreviate the session to get to school on time, and so aborts the session early. If the exercise session continues, step 340 loops back to select a next exercise in step 312. If the exercise session is to conclude, step 340 branches to step 342.

In step 342, the exercise session completes. The exercise session count, stored in NVRAM 143, is incremented. A record of the current time from RTC 144 is stored in NVRAM 143 as a record of the time of the last exercise. If there were any successfully completed exercises, the exercise session count, also in NVRAM 143, is incremented.

Figure 5:
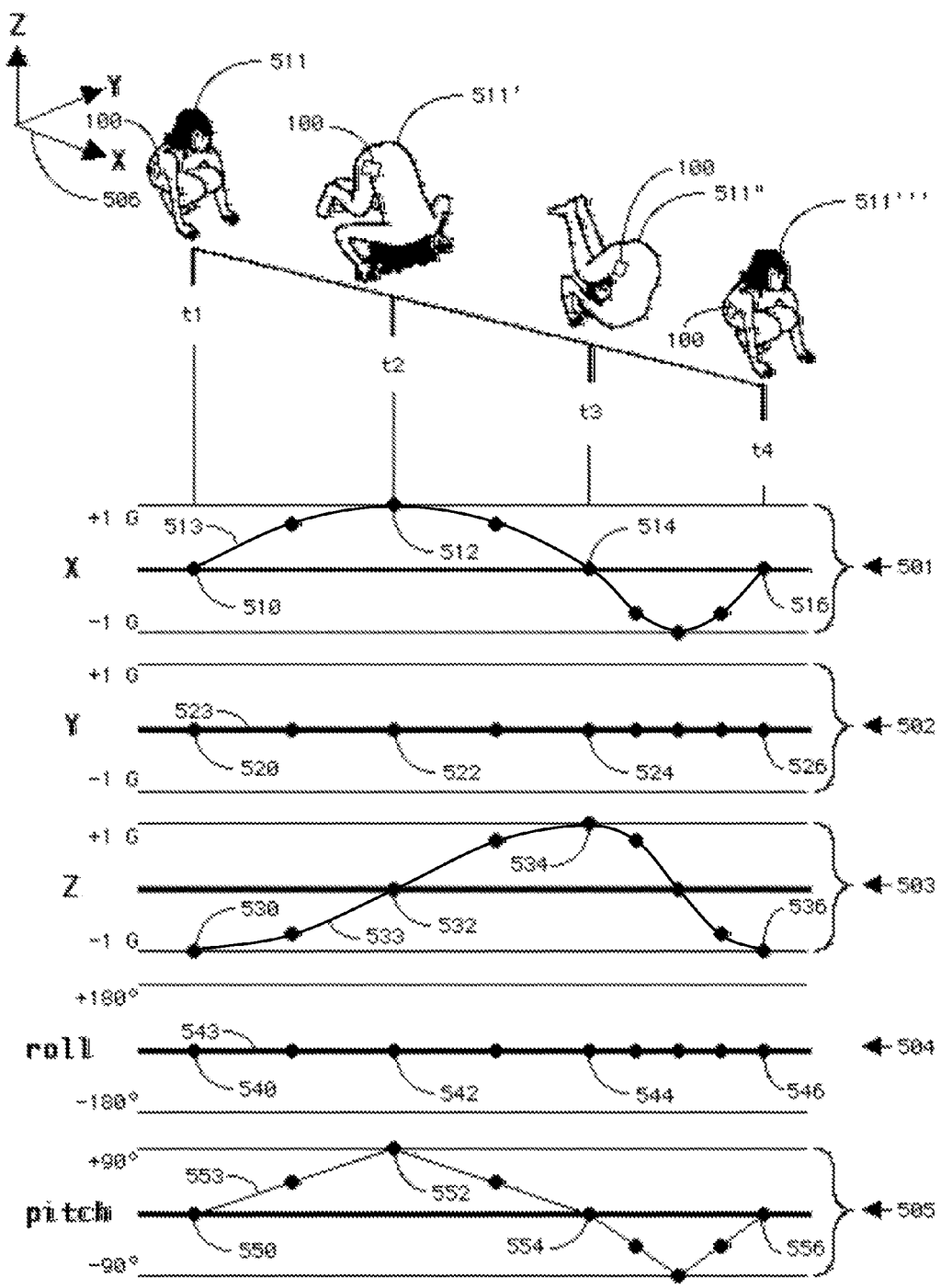
FIG. 5 depicts sample accelerometer waveforms and timing associated with the stages of a somersault.
Figure 6:
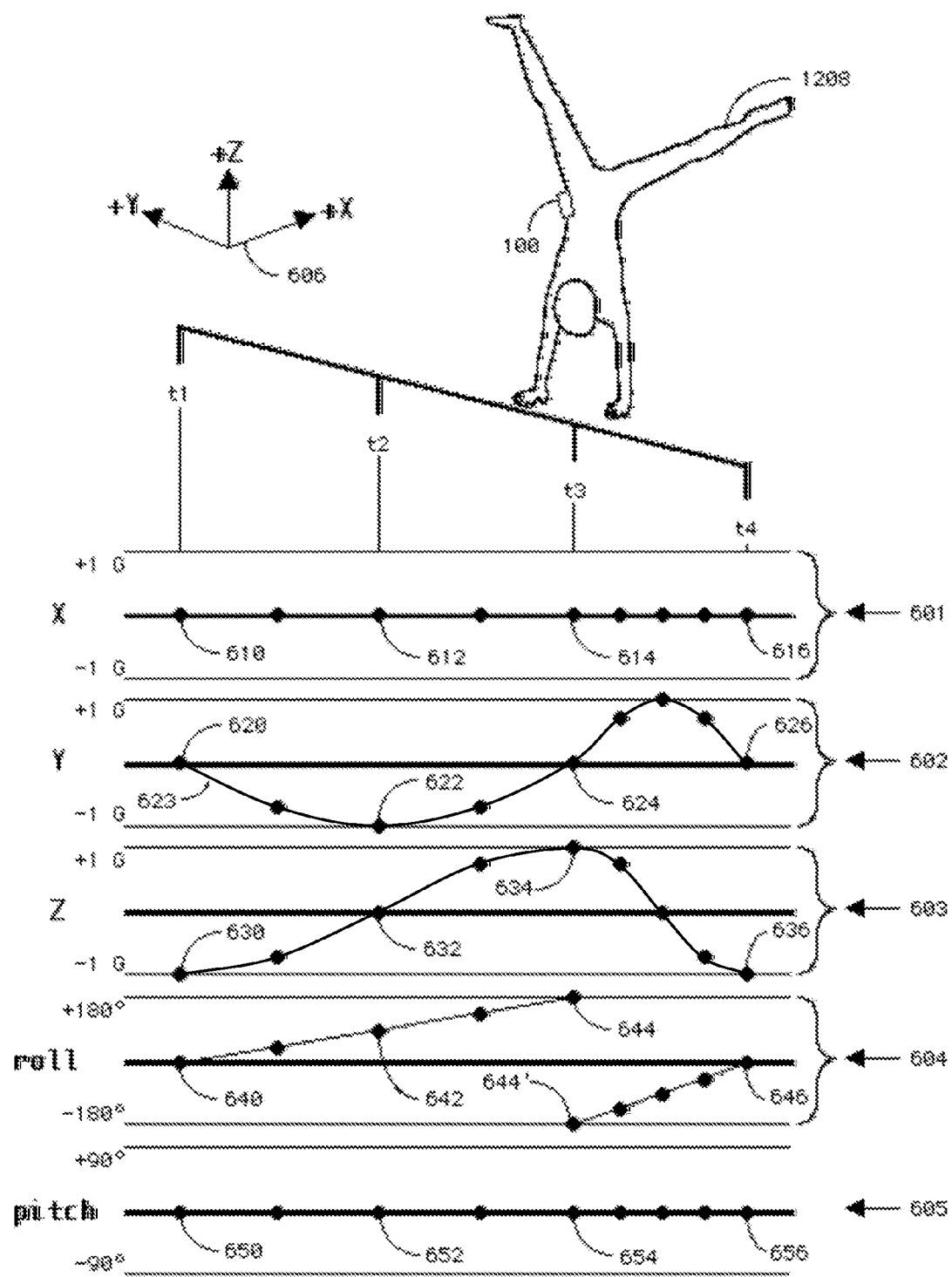
FIG. 6 depicts sample accelerometer waveforms associated with an exemplary exercise (a gymnastics cartwheel)
Figure 7:
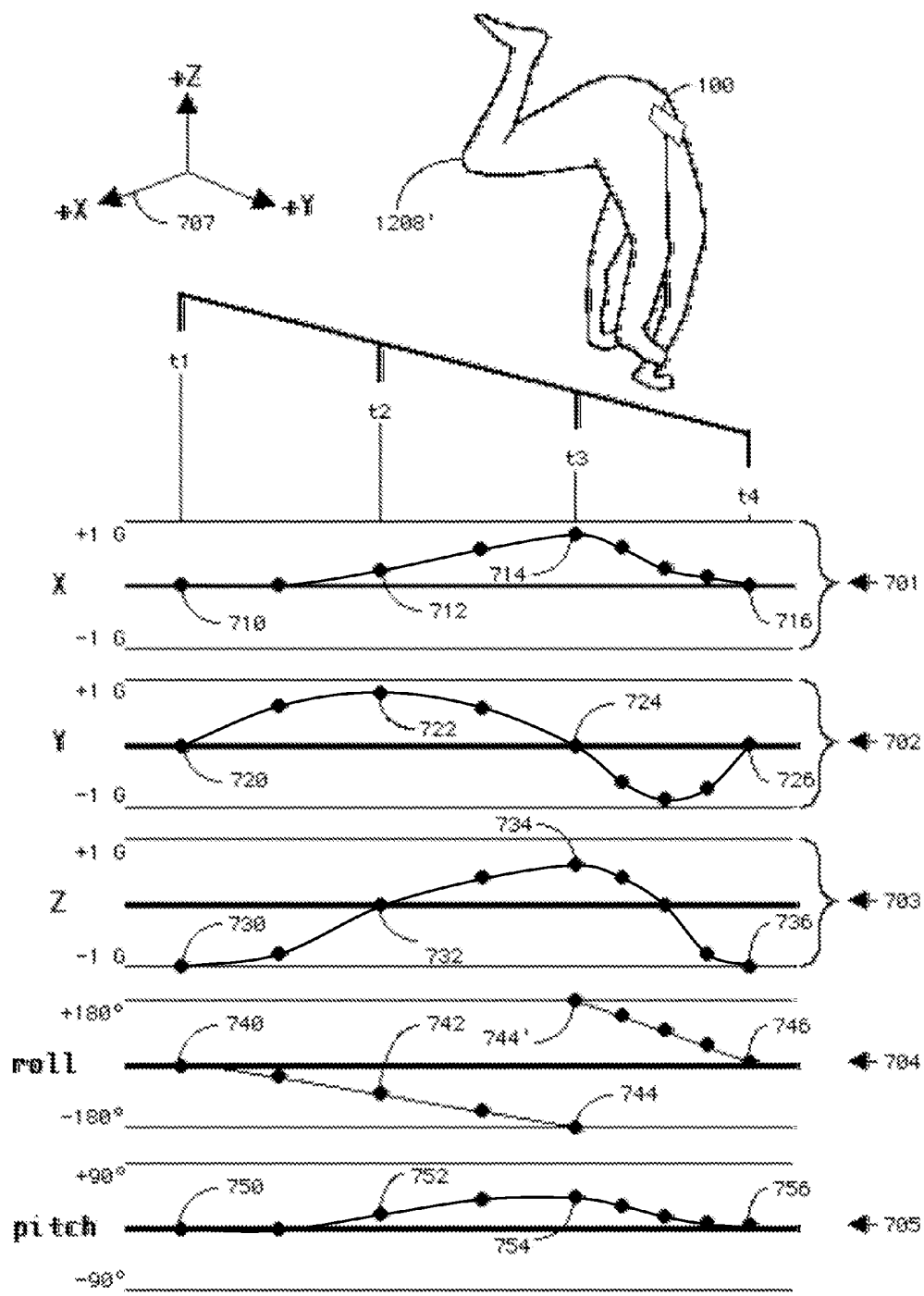
FIG. 7 depicts sample accelerometer waveforms associated with incorrect movements (a failed cartwheel)
Figure 8:
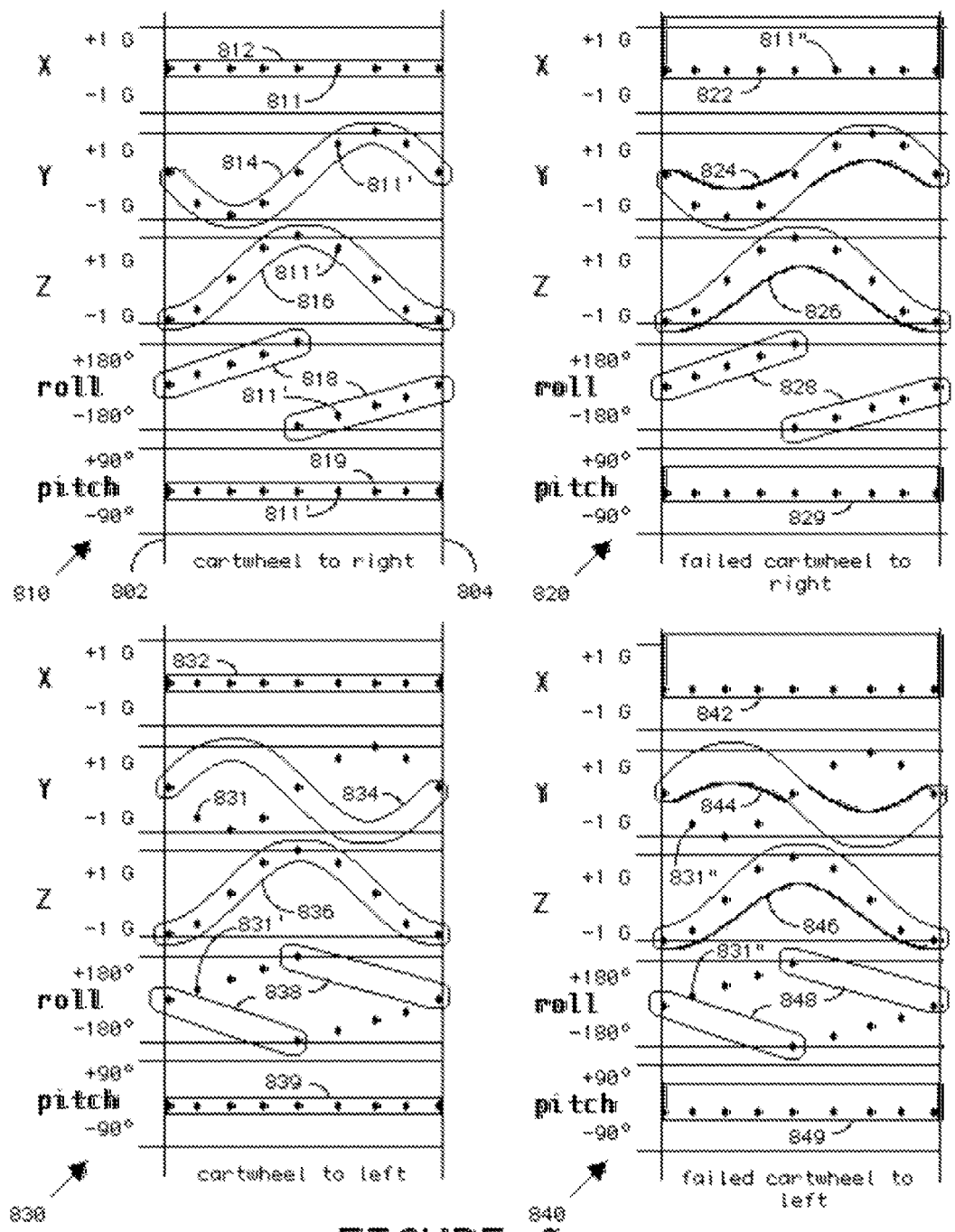
FIG. 8 shows templates for classifying real-time accelerometer data as a successful, failed, or unrecognized exercise execution.

One implementation of sensor monitoring of step 320 is best understood in conjunction with FIGS. 5, 6, 7, and 8. FIGS. 5, 6, and 7 show specific exercises and the sensor readings resulting from them. FIG. 8 shows one embodiment of analysis for implementing step 320, sufficient to distinguish between versions of a specified exercise.

FIG. 5 shows gymnast 511 wearing exercise computer 100. At time t1, gymnast 511 is poised to perform a somersault, which is completed at time t4. Successive transitional postures are seen as gymnast 511', 511'', and 511''' at times t2, t3, and t4 respectively. Coordinate reference 506 show the orientations of the +X, +Y, and +Z axes associated with gymnast 511 at t1. As the somersault progresses, the coordinate frame pitches forward (not shown), generally about the Y-axis.

The acceleration readings throughout the somersault from sensors 149, 149', and 149'', representing the X-, Y-, and Z-axes respectively, are illustrated in the graphs 501, 502, and 503 also respectively.

At time t1, the associated gymnast posture 511 will generate X, Y, and Z readings 510, 520, and 530 respectively. In this posture, the downward acceleration of Earth's gravity registers almost exclusively on the Z-axis in the negative direction. Thus, readings 510 and 520 are approximately zero, while reading 530 is approximately −1.0 G.

At time t2, the posture of gymnast 511' is such that her hips have undergone a right-handed rotation about the Y-axis, which in turn is imparted to exercise computer 100, causing the X-axis to pitch downward. At time t2, the downward acceleration of Earth's gravity registers almost exclusively on the X-axis in the positive direction. Thus, readings 522 and 532 for the Y and Z accelerometers respectively are essentially zero, while the reading 512 of the X accelerometer is about +1.0 G.

Further, a calculation of pitch may be defined as $\arcsin(x)$. The value of x may be the reading on accelerometer 149, in units of G. The result of the pitch equation is a pitch angle in the closed interval of $[-90°, +90°]$. The pitch angle indicates whether the X-axis is pointing downward (a positive angle below the horizontal), upward (a negative angle: above the horizontal), or lying perfectly horizontal (an angle of zero). In this embodiment, x is constrained to lie in the interval $[-1.0, +1.0]$.

In the preferred implementation, x is defined more carefully as the dot product of the vector sum of the readings of the three accelerometers (i.e. the net detected acceleration) and the reading of accelerometer 149. This represents the fraction of the overall acceleration lying in the X direction, and is normalized to the unit sphere, thus x will always lie in the interval $[-1.0, +1.0]$. For the readings indicated in graphs 501, 502, and 503, the corresponding pitch values shown in graph 505 are consistent with both definitions for x. This is also true for pitch data where depicted in FIGS. 6, 7, and 8, described below.

By the above definitions, where the reading 510 of X-axis accelerometer 149 is approximately zero, the X-axis is approximately horizontal, and the net acceleration vector is 1.0 G in the −Z direction; pitch value 550 is approximately zero.

At time t3, the posture of gymnast 511'' is such that her hips, further rotated about the Y-axis, are now upside-down. In this situation, the positive Z-axis is pointing straight down, and the X-axis, though pointing backwards, is approximately horizontal. Gravity now produces reading 534 of +1.0 G in the +Z direction, while the X and Y readings 514 and 524 are approximately zero. The calculated value for pitch 554, is also approximately zero.

At time t4, gymnast 511''' has completed her somersault and is again in the starting posture. As a result, her hips, and therefor exercise computer 100, once again correspond to reference frame 506, and X, Y and Z readings 516, 526, and 536 are approximately identical to readings 510, 520, and 530, respectively. Pitch calculation 556 is approximately that of 550.

Graph 504 illustrates a measure of right-handed roll about the X-axis, however for a somersault, there should be essentially no roll, and thus sample calculations made for values 540, 542, 544, and 546 are all approximately zero. The calculation for roll is elaborated below.

Accelerometers 149, 149', and 149'' can produce a continuum of readings, illustrated by lines 513, 523, and 533 respectively. Similarly, were continuous calculations made for pitch and roll, they would generate continuous lines 553 and 543 respectively. A number of discrete readings and calculations are made at times other than those specifically discussed (t1, t2, t3, and t4), and some of those readings are illustrated as unnumbered dots along those continuous reading lines.

Note that the readings illustrated in graphs 501, 502 and 503 represent filtered accelerometer data. Signals representing substantial resonance in accelerometers 149, 149', and 149'', are filtered out.

Further, the exemplary somersault is considered to have been smoothly performed, a low or moderate speed, without wobbles, hesitations, or sudden movements. The resulting data contains accelerations essentially induced by gravity. Not visible (but present) in reading 510 is a slight acceleration in the positive X direction as the muscles of gymnast 511 propel her forward to begin the somersault. A similarly too-small-to-be-seen acceleration in the negative X direction is a component of reading 516, assuming that gymnast 511''' has come to a stop.

Note that this does not include variations in speed. If time is considered to progress linearly from left to right in the graphs of FIG. 5, then the second half of the somersault (where from t3 to t4 the hips transition from upside-down to right-side-up) was performed twice as fast as the first half (where from t1 to t3 the hips transition from right-side-up to upside-down).

A high-speed somersault, as might be performed as part of an Olympic gymnastics floor exercise, may contain additional accelerations that would be significant. For instance, it is likely the case that during a somersault the gymnast's hips, and thus wearable exercise computer 100, does not maintain a constant altitude. A modulation in the altitude of exercise computer 100 at a slow speed would not represent a significant acceleration, however a modulation at high speed would. The exact nature of such accelerations is best measured empirically.

Additionally, the scale of such modulations may be further dependent upon the size of the gymnast. A given modulation in altitude would scale approximately linearly with the height of the gymnast. In an alternative embodiment, acceleration-altering factors such as height are accounted for by first querying the user for such information. The results of such queries would be stored in NVRAM 143.

The simplest way to accommodate such variations in speed and user body size, is to include additional versions of exercises for analysis in step 320.

Versions of exercises linked to small, medium, and large body sizes would be pre-selected before step 320, based on the user's stored answer to a height query.

Alternatively, height may be estimated based on the exercise versions matched for exercises predetermined to be best for discriminating height. Such a determination would be saved for later use.

Additional versions of exercises would distinguish between slow and fast performances of an exercise. In the case of a somersault, a fast performance may be one of the higher skill level versions discussed in conjunction with step 320 above.

Note that it is not strictly the case that consideration of three body sizes and two speeds would result in six distinct versions of the exercise. At a slow speed, body size may not produce any significant variations, as in FIG. 5. In such a case, additional variations may only be necessary for high-speed performances.

Note that "high" and "low" speed and body sizes of "small", "medium", and "large" are only exemplary. Different exercises will have different dependencies, and more or fewer categories for speed and body size may be appropriate. Again, the exact nature of such accelerations is best measured empirically for the exercises of interest.

In conjunction with FIG. 6, gymnast 1208 wearing exercise computer 100, is performing a cartwheel, leading to his right. Reference frame 606 indicates the initial orientation of the accelerometer axes. Graphs 601, 602, 603, 604, and 605 illustrate the reading of accelerometers 149, 149' and 149" and the calculations of roll and pitch, respectively, from time t1 to time t4.

A well-performed cartwheel will have little or no pitch of the hips. With wearable exercise computer 100 significantly tracking motion of the hips, the X-axis will remain approximately horizontal, and so readings 610, 612, 614, and 616 from X accelerometer 149 will be approximately zero. As a result, the calculations 650, 652, 654, and 656 for pitch will also be approximately zero.

With gymnast 1208 beginning the cartwheel to his right, gravity will read at t1 as a −1.0 G acceleration in the −Z direction, but shift at t2 to a −1.0 G acceleration in the −Y direction. This rotation is a right-handed rotation about the X-axis.

If the starting position of +Z pointing upward is defined as having a roll of zero, then the equation for roll will be arctan 2(−z,−y), where y and z are the readings of accelerometers 149' and 149", respectively. The well-known function arctan 2 is commonly found in software math libraries. It is related to the arctangent function. However, where the arctangent function takes as its single parameter the ratio of the opposite and adjacent sides of a right triangle, the arctan 2 function takes the two sides separately. In so doing, the arctan 2 function is able to distinguish between quadrants I, II, III, and IV of the unit circle, and so can return roll values in the semi-closed interval (−180°, +180°]. The arctangent function can only return values in the semi-closed interval (−90°, +90°].

At t1, with readings 620 and 630, y is about zero and z is about −1.0 G. Roll calculation 640 is about zero. At t2, reading 622 and 632 put y at about −1.0 G, z at about zero, and roll calculation 642 is about +90°.

At time t3, gymnast 1208 is fully inverted, and readings 624 and 634 place y back at zero, but z at about +1.0 G, now the roll calculation 644 is about +180°. At this point, there is a discontinuity in the arctan 2 function. As the reading of Y-axis accelerometer 149' transitions near reading 624 from negative to positive, the pitch calculation 644 will jump from approximately +180° to pitch calculation 644' at approximately −180°. Since the function is discontinuous at this point, intermediate values not near the values of +/−180° will not be seen.

At time t4, gymnast 1208 has returned to his initial posture, and readings 626 and 636 of Y and Z accelerometers 149' and 149" again produce a roll calculation 646 of about zero.

The somersault and cartwheel exercises illustrated in FIGS. 5 and 6 were selected specifically because they largely isolate pitch and roll motions, respectively. Further, they are exercises, which when performed slowly, will have acceleration readings significantly induced by gravity. Other exercises, such as jumping jacks, cannot be performed without significant acceleration readings induced by muscular acceleration and impact. The exercises chosen were selected for clarity of explanation, and are not meant to suggest a limitation to exercises of that type.

In FIG. 7, gymnast 1208' is performing a cartwheel, but is leading with his left hand. Reference frame 707 shows that he began facing in the direction opposite to that of frame 606 in FIG. 6, so that even though he is starting on the opposite hand, his progress from t1 to t4 still proceeds from left to right.

Gymnast 1208' in his left-handed cartwheel is not demonstrating the same quality of form as was demonstrated in the right-handed cartwheel of gymnast 1208.

Specifically, at time t3, gymnast 1208' has not achieved full extension of his legs, and so his hips and exercise computer 100 are pitched. Rather than keeping the X-axis horizontal, as does gymnast 1208, instead the X-axis pitches downward, and a positive reading on accelerometer 149 is seen on graph 701.

In the starting posture, at time t1, graphs 701, 702, 703, 704, and 705 show approximately the same readings and calculations 710, 720, 730, 740, and 750, as are seen in the corresponding elements of FIG. 6.

Since in this exercise, the gymnast leads with the left hand, the Y-axis accelerometer 149' initially trends positive—opposite that of the right-handed cartwheel. At time t2, the Y-axis reading 722 is peaking, and the Z-axis reading 732 is approximately zero (the Z-axis would be nearly horizontal). The roll calculation would indicate a roll of about −90°.

However, in a departure from symmetry with the readings of FIG. 6, the Y-axis reading 722 is not approximately +1.0 G, rather it falls somewhat short. At the same time, the X-axis reading is not approximately zero, but has a small, but noticeable positive value. The gymnast is not headed toward full extension, and his hips are pitched as a result. This pitch is translated to exercise computer 100, and is showing up as a reading on the X-axis accelerometer 149. The pitch calculation 752 quantifies this.

At time t3, the full inversion of the cartwheel should be present, but is not. The Y-axis accelerometer reading 724 is approximately zero, but the Z-axis accelerometer reading 734 doesn't reach +1.0 G—it falls short. Still, roll calculation 744 indicates approximately −180°, which depending on slight variations in reading 724 making it positive or negative, will result in a discontinuous reading 744' of approximately 180°. The X-axis accelerometer, however, shows a strong, positive reading 714 that corresponds to pitch calculation 754.

At time t4, the gymnast has returned to his starting posture, and readings 716, 726, 736, and calculations 746, and 756 correspond to the original values at t1.

FIG. 8 shows a collection of exercise templates 810, 820, 830 and 840 used to monitor sensors 149, 149', and 149". Each exercise template corresponds to a single version of a specified exercise. In this example, the specified exercise is a cartwheel. Such specification would occur in step 312, and the exercise templates 810, 820, 830, and 840 would be activated. Exercise templates related to other exercises (not shown), such as a somersault, would not be active and would not be used in step 320. (In the alternative embodiment discussed above, wherein step 312 is bypassed and no selection is made, all exercise templates would be active.)

Exercise template 810 is designed to detect a cartwheel starting on a gymnast's right hand.

Exercise template 810 is comprised of value templates 812, 814, 816, 818, and 819 for the X-, Y-, and Z-axes, roll, and pitch; respectively. In particular, value templates 812 and 819 require that readings for the X-axis accelerometer 149 and results of pitch calculations, respectively, remain near zero. Value template 814 requires that readings for the Y-axis accelerometer 149' begin near zero, trend initially negative to near −1 G, then proceed through zero to near +1 G, and finally return to approximately zero. Value template 816 requires that readings of the Z-axis accelerometer begin near −1 G, proceed through zero to approximately +1 G, and return to reading approximately zero. Value template 818 requires results from roll calculations to begin near zero, progress with a positive trend to +180°, transition discontinuously to about −180°, and resume the positive trend to return to approximately zero. Note that the discontinuous transition from +180° to −180° is not required to be monotonic. Since the two halves of value template 818 are not mutually exclusive as progress is made from left to right, this template accommodates noise in the Y-axis signal that may cause the roll calculation to vacillate momentarily between +/−180°.

Resulting from the performance of a selected exercise, a set of readings is collected from the X-, Y-, and Z-axis accelerometers. Along with the corresponding calculations for roll and pitch, these values are illustrated as dots, such as 811. The same set of values is represented overlaid on each of the exercise templates 810, 820, 830, and 840.

The simultaneous values from readings and calculations are kept in a vertical line. For example, reading 811 is essentially simultaneous with the readings and calculations 811'.

In an alternative embodiment, where readings and calculations were substantially non-simultaneous, later readings would be displaced slightly to the right.

The set of current values of readings and calculations are applied to active exercise template 810 beginning at start line 802. If, for exercise template 810, all current values fall within the bounds of each corresponding value template 812, 814, 816, 818, and 819, then exercise template 810 is said to be running. The progress of a newly running exercise template is set to 0%, that is, the progress corresponds to start line 802. A progress of 100% is represented by the finish line 804.

As each successive set of values is acquired, analysis proceeds monotonically, from left to right, toward finish line 804 on each running exercise template. Analysis of the successive set of values for each running exercise template entails finding the leftmost progress value to the right of the previous progress value for which all of the most recent values remain within the value templates. This analysis is further constrained by disallowing a large change in progress.

In the preferred embodiment, changes in the progress values for a running exercise template would be limited to some fraction of the full progress scale.

For instance, somersaults and cartwheel exercises would easily tolerate a maximum incremental progress limit of 10%, and will usually work with a limit of 20%, even if successive value sets were provided at 10 Hz. For comparison, the sample dots shown in FIG. 8 are uniformly distributed at about 12.5% progress intervals. The actual percentage limit should be determined empirically, and may vary for each exercise, or even for each version of each exercise.

In an alternative embodiment, the percentage limit may vary within each exercise template. For instance, if for a certain region of an exercise template, all value templates represent slowly changing values, then the maximum change in percentage progress might be larger. Conversely, if one or more of the value templates represents rapidly changing values, then the maximum change in percentage progress might be reduced.

Percentage progress and the maximum rate at which progress is allow change should not be confused with the rate at which readings are taken, though the two are related. If an exercise template is analyzed with a maximum progress rate of 10%, then that exercise cannot be detected with fewer than 10 sets of simultaneous readings and calculations. The first set of values would set the exercise to running, progress would be set to 0%, and each successive reading could proceed toward completion, 10% at a time.

In step 322, the determination of whether an exercise has been detected is preferably achieved by examining, for each running exercise template, whether both of the following two conditions are met. The first condition is whether the progress level for the running exercise template is within the allowed maximum increment of the finish line, i.e. is the current progress plus the maximum progress increment greater than or equal to 100%. The second condition is whether the most recent set of simultaneous values, if held continuously from the current progress level to the finish line 804 would continuously remain within the associated value templates. If both conditions are met, then the running exercise template is transitioned to the status of "complete".

In an alternative embodiment, a minimum progress increment may be specified, too. With both a minimum and a maximum incremental progress specified, in conjunction with a specific rate at which readings are taken, and as long as the minimum progress is non-zero, a specific exercise template would constrain that a specific version of an exercise would have minimum and maximum allowable execution time. If the minimum progress allowed were set to zero, for all or part of an exercise template, then progress in the performance of that exercise could be held indefinitely, subject to the timeout constraints implemented with step 330. This would be particularly useful for exercises where holding an intermediate position for as long as possible is valuable, e.g. pausing partway through a sit-up.

Further, differences in minimum progress values can be used to differentiate between versions of an exercise. A sit-up performed at a regular rate might be considered an intermediate performance, whereas a sit-up performed where the strenuous portions are performed slowly might be considered as a superior performance, as might be sit-ups performed rapidly.

Performing cartwheels at a rate of one per second would be exceptional. However, at expert levels, performing exercises at such a rate is feasible. In such a case, simply setting minimum or maximum progress rates allowed for each set of successive values is not entirely sufficient. The rate at which readings are taken and calculations are performed to get sets of successive values with sufficient frequency is also required to capture of faster versions of exercises. Even if these frequencies are determined to be 20 or 30 Hz, or faster, such data rates are well within the capabilities of common accelerometers and associated circuitry.

Many alternatives are available for the encoding and processing of value templates. Rather than envelopes, such as the one implementing value template 814, an alternate value template implementation would be to encode the value template as a curve (not shown), running from start line 802 to finish line 804. Such curves would correspond roughly to the centerline of the envelope. For value template 814, a curve-based implementation would be similar to continuous value line 623, though the arbitrary distortions of performance speed present in continuous value line 623 would be smoothed out and idealized in the template version, as was done for value template 814. In this alternative curve implementation, a curve can be discontinuous and multi-valued. A curve that could implement value template 818 would have a similar discontinuity, and in proximity to that discontinuity, would have dual values near +180° and −180° for the same progress level. Successive evaluations of progress would seek rightward for a best fit of the current set of values to the curves. A least squares fit would suffice, and may be constrained to maximum (and minimum) progress rates, as above.

If any one of any successive set of values fails to fall within a value template, the exercise template fails, returning to a status of "not begun". This is illustrated in exercise template 830.

Exercise template 830 detects a cartwheel starting on the left hand, and is comprised of like-related value templates 832, 834, 836, 838, and 839. The values of readings and calculations in the first column match exercise template 830 and would induce it to a status of "running", with a progress of 0%. In the next column of values, reading value 831 of Y-axis accelerometer 149', does not fall within value template 834, unless the progress were advanced to about 62%, which would exceed a 20% maximum incremental progress limit. Similarly, computation value 831' does not fall within value template 838 unless the progress was advanced to about 88%, which also would violate a 20% maximum incremental progress limit. The remaining values in the same column fit within their respective value templates 832, 836, and 839. However, since no allowable progress value can be found that keeps all of the current values within their respective templates, as of the second column of values, exercise template 830 transitions from "running" to "not begun".

Exercise template failure, in the alternative embodiment where value templates are encoded by curves, will occur whenever the least squares fit of the current set of values to the value template curves for an exercise template exceeds a predetermined value. Alternatively, the exercise template will fail if any one of the set of values deviates from the corresponding curve by more than a predetermined amount.

Exercise template 840 shows a template that will accept an exercise performance of a cartwheel led with the left hand, as depicted in FIG. 7. As discussed with respect to graph 701, the deviation from the performance of an ideal cartwheel was largely exhibited in the significantly positive-going X-axis reading, corresponding to the aberrant pitching of the hips. In exercise template 840, the value template 842 for the X-axis accelerometer 149 is extended in the positive direction, relative to value template 832. A similar extension of value template envelope 849 in the positive direction, as compared to value template 839, accommodates the positive pitch for a failed performance in this mode, as at pitch value 754.

Value templates 844 and 846 are slightly wider in places, to admit lower peak readings of the Y- and Z-axis accelerometers, 149' and 149" respectively. The lower peak readings 722 and 734, seen in graphs 702 and 703, are a side effect of the pitched hips in a failed performance in this mode. The value template 848 for roll, however, is roughly the same, since the measurement of roll for this exercise is largely unaffected by the amount by which a gymnasts hips pitch.

Even with the increases in the value template envelopes of exercise template 840, the set of values in the second column still including values 831" which cannot fit into their respective value templates for acceptable progress values. Hence, for the same sequence of readings, exercise template 840 also transitions to "not begun", as the sequence of reading and computation values do not match the corresponding value templates.

In exercise template 820, analogous expansions of value templates 822, 824, 826, and 829 are seen. Here, each successive set of values remains entirely within the value templates, and so for the sets of values shown, exercise template 820 will transition along with exercise template 810 from "running" to "complete" in step 322. In step 324 the completion of "correct" exercise template 310 will be detected, and in step 334 any exercise templates with a "running" or "complete" status will be reset to the status "not begun".

A race condition may exist, due to slight variations in value templates inducing varying rates of progress within related versions of an exercise. It is possible that the progress of one failed version of an exercise moves marginally ahead of the ideal version of the exercise. In such a situation, it is possible for an exercise template for a failed version of the exercise (e.g. 820) to complete in step 322 and be detected in step 326, a reading or two before an exercise template for a correct version of the exercise (e.g. 810). To prevent such a race condition from inappropriately blocking acknowledgement of a successful performance, step 326 can stall the recognition of incorrect pattern recognition by branching (not shown) to step 330 until the pattern completion is aged for one or two more iterations. This would allow a nearly completed detection of a correctly performed exercise to be recognized. Step 326 might forgo this delay, if no correct exercise templates are appropriately close to completing, i.e., have a progress value within one or two progress increment of the finish line.

Exercise templates 810 and 830 (likewise 820 and 840) have similar value templates for the X-, Z-, and pitch axes, and have inverted Y- and roll axes. Alternative implementations can take advantage of such commonalties and symmetries to achieve efficiency in computation and storage. For clarity, that is not shown here. The similarities of value templates 828 and 848 to value templates 818 and 838, respectively, and their mutual symmetries, could be used to gain similar efficiencies.

The pattern matching mechanisms illustrated in FIG. 8 can be replaced by any of a number of well-known pattern recognition techniques. Those skilled in the art will recognize the applicability of fuzzy logic, expert systems, and neural nets. These and many other techniques can be brought to bear on the task of identifying the performance of an exercise from the time-history of sensor readings and derivative calculations.

Since the development of exercise templates for a large number of exercises represents a significant empirical process, the ability of neural nets to produce a self-organizing system in response to pre-adjudicated data sets is valuable. In one alternative embodiment using neural nets, for each exercise of interest, sensor measurements of many separate performances would be recorded. The judgement of an appropriate authority (e.g., a sports trainer) would indicate whether each performance was good. If not, the authority would classify the failed performance as a particular mode of failure for which specific remedial instruction would be appropriate. At the least, a skill grade should be given for each performance. Similarly, exceptional performances might be identified and given high skill grades. A notation in each of the recorded performances as to the height of the performer, would enable the resulting network to consider height as a parameter for distinguishing between exercise templates. With a sufficient number of recorded and judged performances, and a topology of neural net nodes, the neural net training process can proceed. Both the number of performances required and the topology of the neural net to be used are best determined by an expert in the field. The desired result for each exercise is neural net that will accept a time-series of accelerometer values (and possibly derivative calculations) and indicate when one or more versions of the exercise have been performed. An indication of skill grade for a performance can also be given.

Rewarding Exercise Performance

Figure 9:
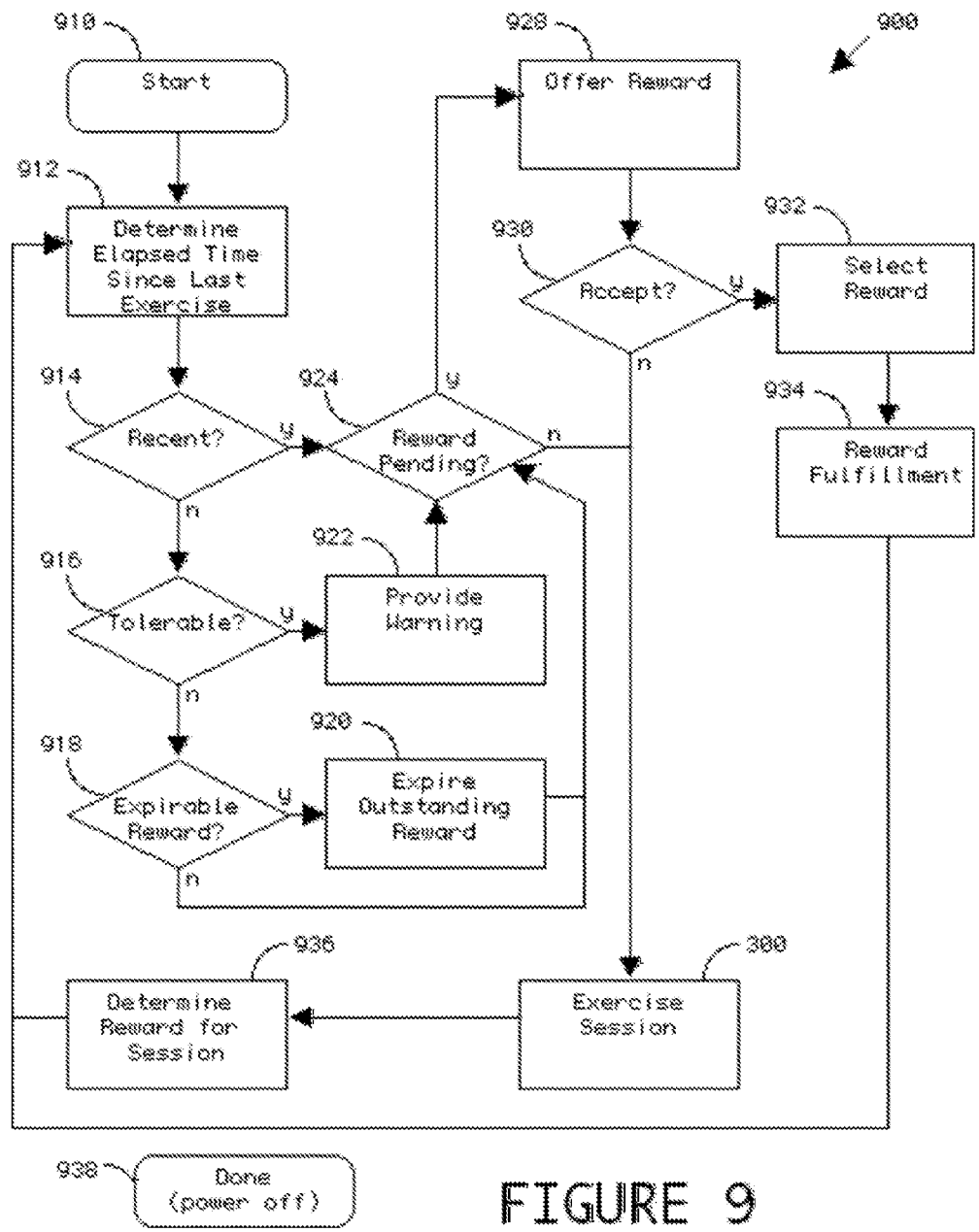
FIG. 9 shows a flowchart for a procedure to entice a user to maintain an exercise regimen over a long-term.

Referring to FIG. 9, the preferred embodiment of reward process 900 is shown. Integral to reward process 900, is monitored exercise session 300.

In step 910, the reward process is initialized. If earned reward database 1020 is not initialized, as on the first execution of process 900 in cartridge 140, then the database 1020 is initialized, preferably with no records 1030 and 1030'.

Alternatively, one or more initial rewards could be made available, for example as demonstrations. Each of these would be represented by a reward record 1030 in reward database 1020.

Also, on first execution, a location in NVRAM 143 for storing a point count (discussed below) is zeroed.

On first execution of process 900 in cartridge 140, then RTC 144 should be initialized. This is understood to be easily achieved using a simple clock and calendar setting user interface, and this activity would be necessary should it be desirable to use exercise computer 100 as a timepiece or calendar.

Alternatively, however, process 900 utilizes RTC 144 for elapsed time and day information, and the RTC 144 can be simply zeroed (set to its minimum date and time), or otherwise set to a valid, usable value. This preferred automatic process requires no user intervention.

Most preferably, the setting of RTC 144 is achieved automatically when exercise computer 100 is connected to server 180 through personal computer 160 and connection 150. If this is the case, then the previously described automatic process can be used initially, then when a connection to sever 180 occurs, the difference between the current value of RTC 144 and the new setting from server 180 can be added to all records of prior RTC values made under the automatic setting, thus correcting them to correspond with the current time supplied by server 180.

Also, if this is the first execution of process 900 in cartridge 140, then the storage location in NVRAM 143 representative of Date of Last Exercise (not shown) should be initialize to a value representative of "never". Another storage location representative of Next Exercise Session Number is set to one.

As a check, if this is not the first execution of process 900, the current value of RTC 144 should be greater than or equal to Date of Last Exercise stored in NVRAM 143. If it is less, then battery 145 has failed and either battery replacement is needed, or has been performed. A warning should be presented to user 819 via display 124. An optimistic, automatic recovery technique would be to set RTC 144 to the value stored as Date of Last Exercise, plus a day. However, this will ultimately represent a method of cheating the system. Alternatively, if the clock and calendar setting user interface previously mentioned was originally used, it should be used again. Most preferably, the RTC 144 is set by communication with server 180 when connected to personal computer 160 via connection 150.

After initialization, step 912 evaluates the amount of time elapsed since the previous exercise session. This can be computed as the difference between the current value of RTC 144 and the value stored in NVRAM 143 as the Date of Last Exercise. If the Date of Last Exercise is "never", then elapsed time can be considered as zero.

In step 914, the resulting elapsed time is tested for being recent. If the previous exercise session had occurred, for example, within 48 hours (two days), then it would be considered recent and any pending rewards would be offered in step 924.

If, however, the elapsed time does not indicate a sufficiently recent exercise session, then it is tested for being tolerable. If the previous exercise session had occurred, for example, within 72 hours (three days), then it would be considered tolerable. In this case, in step 922 a warning would be shown on display 124, informing the user that if exercise sessions are too infrequent, then previously earned rewards will be withdrawn. Any pending rewards would be offered subsequently in step 924.

If the elapsed time further does not indicate a tolerably recent exercise session, then preferably some, but in the alternative, all, pending rewards may be expired. Step 918 tests for the existence of rewards having records in database 1020. An earned reward in reward record 1030 is expired by setting expired flag 1037 in step 920. Preferably, rewards having an expiration date 1036 are not expired in this way, since they have another expiration mechanism. If an earned reward is expired, it may also be marked as renewable by setting the renewable flag 1034. Elsewhere in process 900, the opportunity to renew this now-expired reward may be made. Having completed the reward expiration steps 918 and 920, pending rewards (if any) are offered in step 924.

In step 924, any pending rewards are identified for presentation to user 819. For a successful user, this would compile a list, possibly hierarchical, of non-expired rewards in reward database 1020.

Preferably, before the list is presented, step 924 deletes from database 1020 any rewards having an expiration date 1036 that is less than the current value of RTC 144. An example of a reward having a specific expiration date would be an electronic manufacturer or vendor's coupon 1300 (discussed below in conjunction with FIG. 13) representing a limited time offer.

If no rewards are found pending in step 924, a message (not shown) to user 819 may be shown on display 124 to remind him of the kinds of rewards that can be obtained. Exercise session 300 is started, to allow user 819 to earn rewards as promised.

Upon completion of exercise session 300, step 936 performs an analysis of all exercise records in exercise history data 1000 having a session number 1012 that matches the Next Exercise Session Number in NVRAM 143.

The analysis of the exercise records matching the Next Exercise Session Number determines whether the exercises in newly completed exercise session 300 qualify for a reward. Preferably, each selected exercise successfully completed by way of step 338, corresponds to a point value that is preferably a function of the exercise ID 1011, the skill grade 1013, the skill expected 1014, the repetitions 1015, the requested repetitions 1016, the actual elapsed time 1017, the target time 1018, or a combination thereof. Awarding points for task performance is a field well established in the domain of computer games, and familiar to those skilled in the art. Alternatively, a single point may be awarded for each exercise successfully completed by way of step 338.

In an alternative embodiment, one or more points may be awarded in the same manner for incomplete performance of exercises by way of step 344. Here, the point value will be inferior to that obtained for exercises completing by way of step 338.

Preferably, points for exercises completed are tallied by incrementing the point count at a location in NVRAM 143. Such points preferably represent a proto-reward, which do not directly create an earned reward record 1030, but which accumulate until some or all of the accumulated points are converted into a reward. The award of these points may be displayed to acknowledge the progress user 819 is making toward achieving an actual reward.

In an alternative embodiment, these points can be recorded in a rewards earned record 1030 with a reward ID 1031 that indicates special treatment: In step 922, accumulated points would be decreased by some predetermined amount; and in step 920, accumulated points would be decreased by a larger amount, preferably based on the number of days elapsed since the Date of Last Exercise. In this way, the points take on a behavior similar to and symbolic of the benefits of exercise, which diminish when not maintained with sufficient frequency. For this embodiment, a Date of Last Expiration is stored in NVRAM 143 by storing the current value of RTC 144. In subsequent executions of step 920 or 922, if the Date of Last Expiration is more recent than the Date of Last Exercise, then the decrease in accumulated points will be made only for the interval since the Date of Last Expiration.

In another embodiment, points may not be so clearly, nor so immediately indicated. This would help to conceal the algorithm for their award from the user. Otherwise, instant and detailed feedback may aid in the development of effective cheating methods.

Returning to step 924, if there are rewards pending, or if there are sufficient points that could be redeemed for a reward, then step 924 branches to step 928.

In step 928, pending rewards are offered to user 819. Preferably, there are three categories of pending rewards: those that can be purchased by redeeming some or all of the user's points; those that have already been so purchased and are not expired; and those that have already been so purchased but which have been renewably expired.

Rewards that can be purchased by redeeming some or all of the user's points would be shown in a list, along with the number of points needed to acquire them. Additionally, other rewards which cannot be purchased at this time, because they require more points than are presently available, may be displayed to entice user 819 to earn more points through continued or greater achievement. In the simplest embodiment of the invention, such rewards are stored locally in ROM 142 and are being "unlocked". In an alternative embodiment, rewards may come from server 180, as discussed below in conjunction with FIG. 12.

Separately, non-expired rewards that were previously purchased are listed, and are immediately available for user 819 to enjoy, as described below.

If any rewards that have been previously purchased were subsequently expired in step 920, they are listed as being available for renewal. Renewal of an expired reward requires far fewer points than the original purchase, but motivates and disciplines user 819 to maintain his exercise regimen. By making reacquisition of previously purchased rewards easier than their original acquisition, user 819 is better motivated to resume his exercise program, otherwise he is walking away from a larger historic investment.

In step 930, if user 819 declines to accept the rewards offered in step 928, a new exercise session 300 is initiated. However, if he chooses to accept one of the rewards offered, then in step 932 he indicates which of the offered rewards he wants.

In step 934, user 819 receives fulfillment of the selected reward, discussed below with respect to FIGS. 11, 12, and 13. Specifically, if the selected reward is resident in ROM 142 or, in a previous step 934, has been previously obtained and stored in flash 147 (as described below), step 934 merely represents allowing user 819 to enjoy his reward (e.g. play a game). However, if the selected reward is currently external to wearable exercise computer 100, for example it resides on server 180, or on a CD-ROM (not shown) to be read by personal computer 160, then step 934 will first entail loading the reward into flash 147.

Note that fulfillment of a reward may occur over multiple invocations of step 934. For instance, in one invocation, a reward may be loaded into flash 147. In a subsequent invocation, the reward is used (e.g., a game reward is played). In still another invocation, the reward is used again, providing it does not expire.

When step 934 concludes (e.g., user 819 has quit the game selected as the reward), process 900 returns to step 912. This loop will repeat indefinitely, until broken by powering off wearable exercise computer 100, in step 938. Upon resumption of power, the process preferably resumes at step 910.

Figure 10:
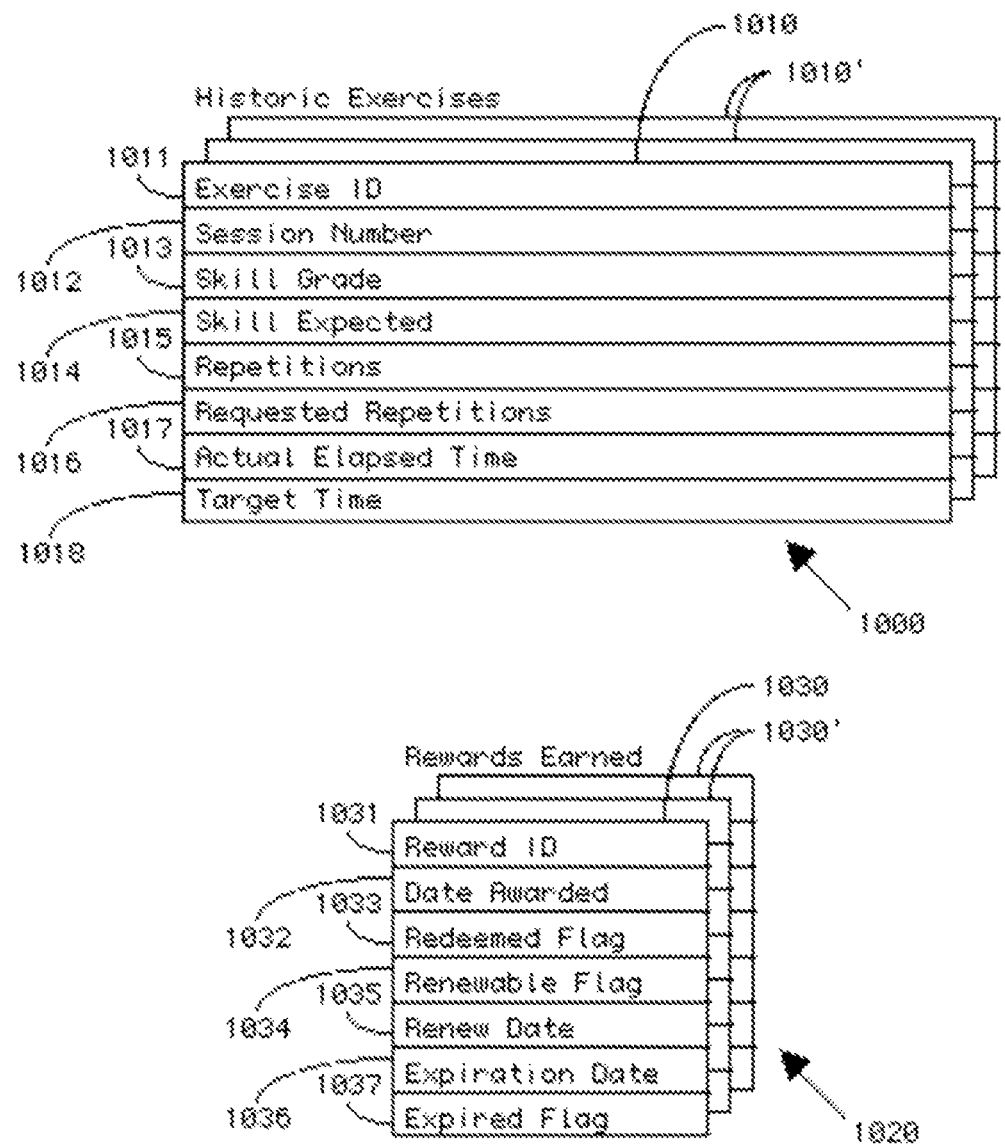
FIG. 10 shows a data record templates for noting the historic performance of specific exercises and rewards earned.

With respect to FIG. 10, those elements not already discussed are described below in conjunction with other FIGURES.

Figure 11:
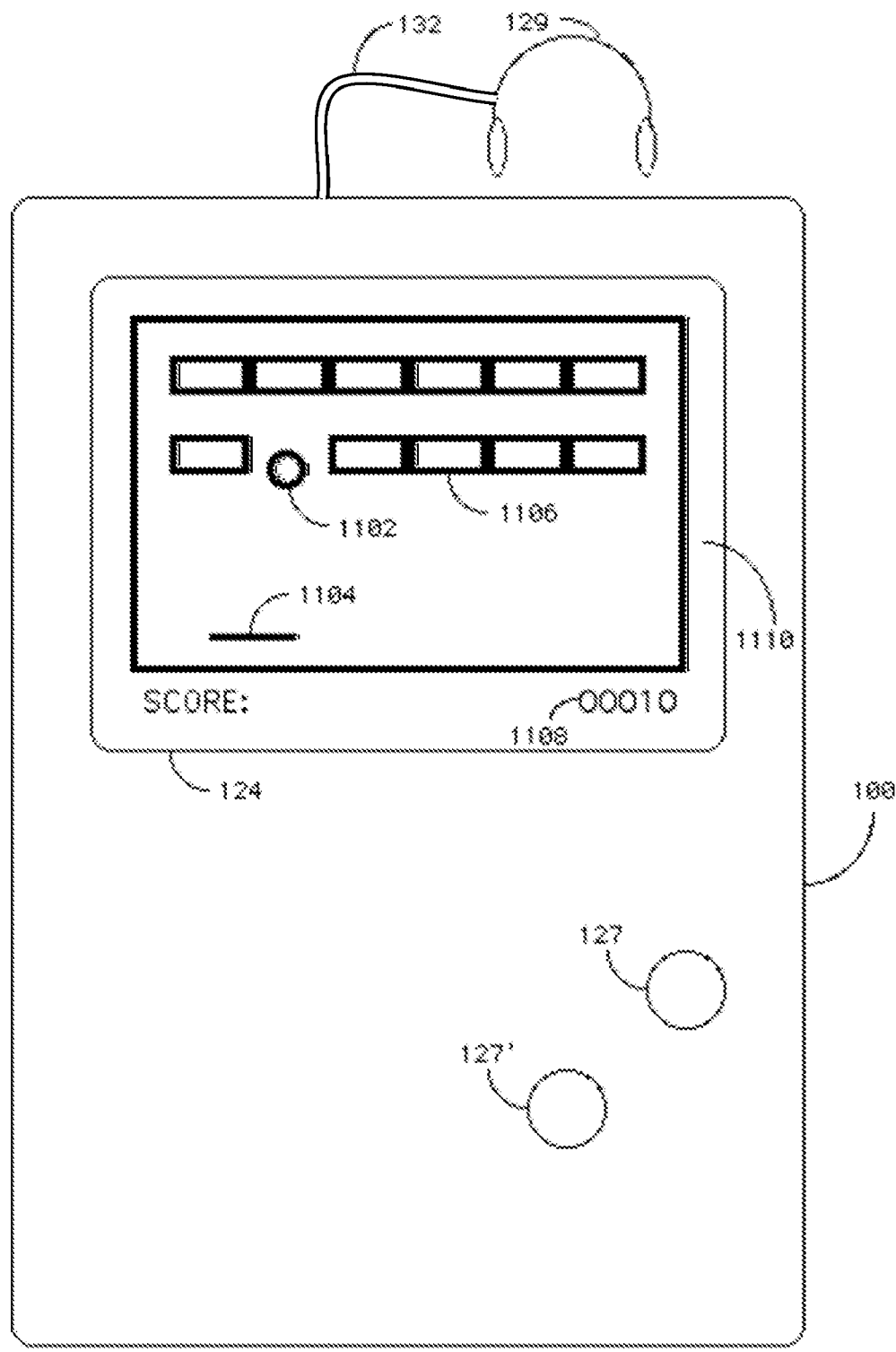
FIG. 11 shows a display screen showing a selected reward, a built-in game.

In FIG. 11, display 124 is showing a game 1110 having a paddle 1104 controlled by buttons 127 and 127' for inducing ball 1102 to destroy bricks 1106, thereby building score 1108. Game 1110 is representative of a video game used as a reward.

Further, other rewards popular with children, such as music and video, especially cartoons, could be provided in a similar manner. Video would be stored as rewards on wearable exercise computer 100, preferably in flash 147. Further, the video is preferably prepared using a compression algorithm for efficient storage. Subsequently, the stored video is decoded for playback on display 124 and audio output 128. A commercial example of such video compression and playback technology is the series of cartoons provided for Nintendo's GameBoy® Advance by Majesco Games of Edison, N.J. Similarly, music, preferably compressed as MP3 files, and preferably stored in flash 147, would be decoded by CPU 121 for playback through audio output 128, headset connection 132, and headset 129.

Rewards such as music, video, or game 1110, might be built into ROM 142, or downloaded as files from server 180 and stored in flash 147. Alternatively, a reward might be loaded as files from a CD-ROM or other media (not shown) to be read by computer 160 and stored in flash 147.

Figure 12:
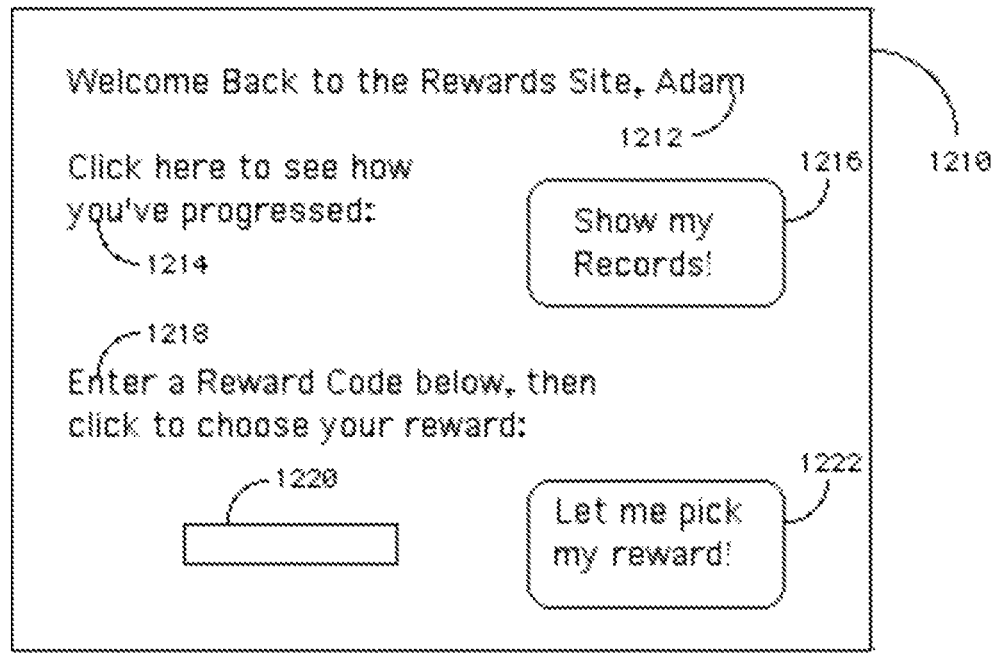
FIG. 12 shows exemplary Internet browser screens for enabling a handheld computer to access a selectable, downloadable reward via a personal computer.
Figure 12:
Figure 13:
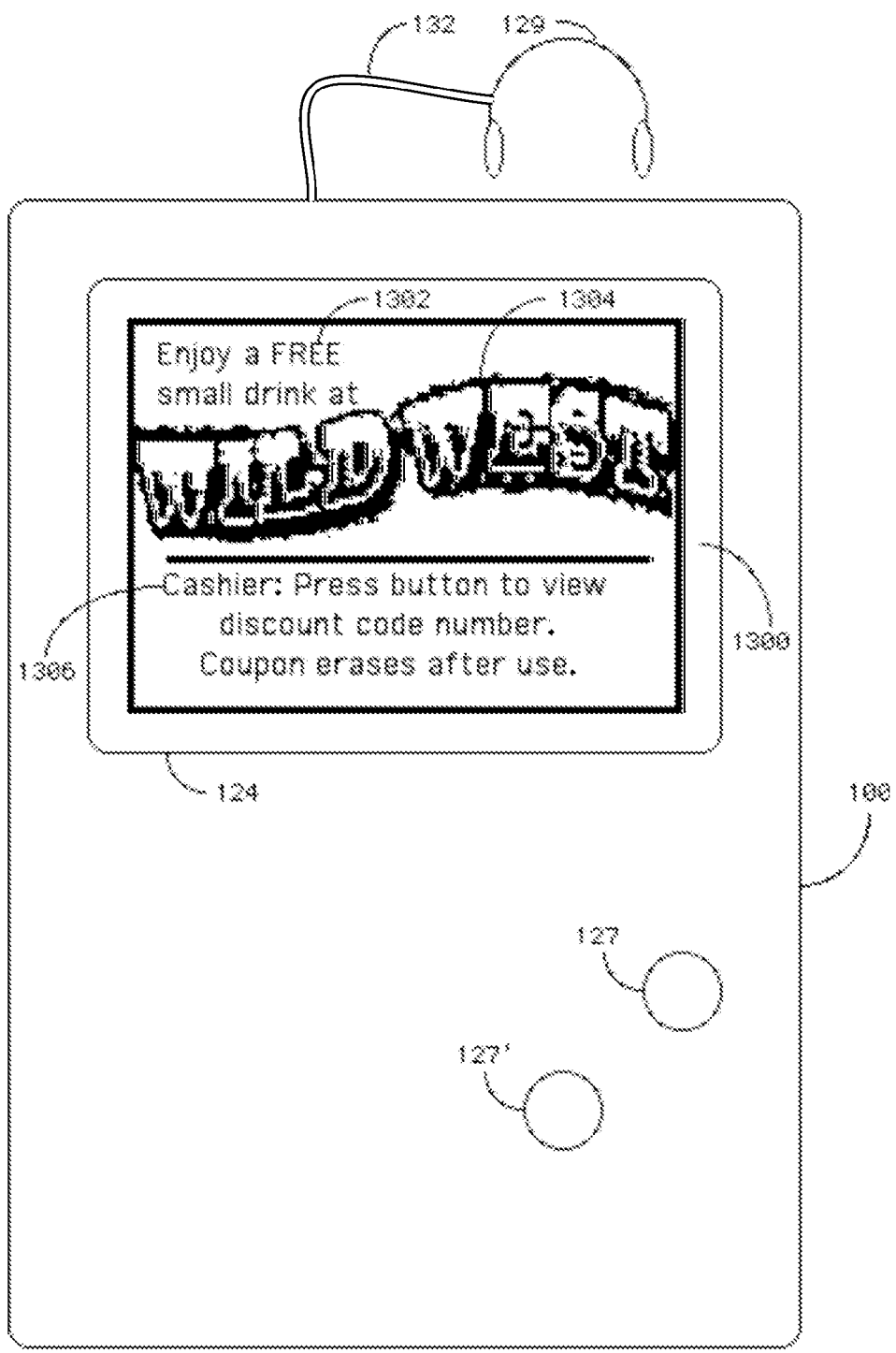
FIG. 13 shows an exemplary display screen showing an electronic reward coupon.

The download of rewards as files from server 180 is preferably achieved in conjunction with a web site, selected pages of which are illustrated in FIG. 12, as screens 1210 and 1230.

Screens 1210 and 1230 presume that user 819 has an account on server 180. Creation, maintenance, and access to such accounts are well known and not illustrated here. Account creation requires the association of unique username 1212, a password, and other data specific to user 819, described below. Account creation is preferably achieved with through an account creation web page (not shown), as is typical in the art. However, in an alternative embodiment, the account may be created by telephone or by mail through an interaction with a customer service representative.

Figure 14:
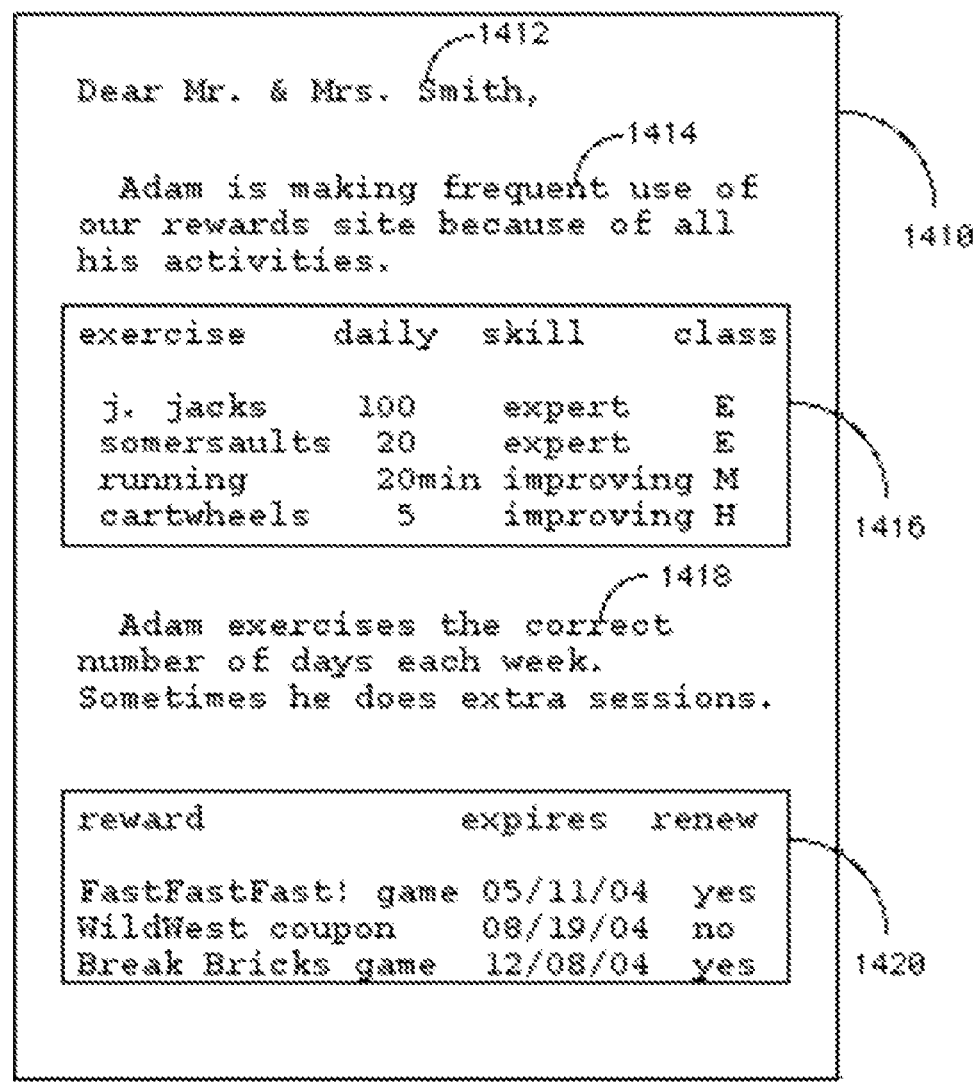
FIG. 14 shows an exemplary report provided to a child's parents.

A customary web site login page (not shown) which, upon receipt of a user-entered username 1212 and password, allows access to the account of user 819. Upon successfully logging into the account of user 819, historic exercise data 1000, and optionally all or part of earned reward database 1020, are uploaded to server 180 for subsequent reporting, described in conjunction with FIG. 14.

Preferably, wearable exercise computer 100 possesses an ID code (not shown) of some sort. For example, the ID code may come from CPU 121 having a unique identifying serial number, available for reading by a processor instruction. Alternatively the ID code may be obtained from cartridge 140, which may include a machine-readable hardware serial number (not shown, though potentially a functionality supplied by RTC chip 144, for example the DS1688 manufactured by Dallas Semiconductor, Maxim Integrated Products, of Sunnyvale, Calif.) that can be accessed through bus 141. In another alternative embodiment, ROM 142 might be programmed with the ID code, such that a particular location contains a unique or infrequently duplicated value. In another embodiment, the ID code is stored in a portion of flash 147 or NVRAM 143 set aside to indelibly store the unique or infrequently duplicated value. In the case of an ID code coming from a hardware serial number (from CPU 121 or other chip) or value in ROM 142, the ID code is established at the time the corresponding chip is manufactured. In the case of the value being stored in flash 147 or NVRAM 143, the ID code may be established at the time cartridge 140 is manufactured, or the ID code may be established by selecting and storing a random value at the time cartridge 140 is first activated (e.g. a 16-bit value obtained by taking the last 16 bits of the real-time clock value at the time of first activation).

The ID code has two distinct uses with respect to server 180. The first use for the ID code, applicable if the ID code is unique, is for web site login to the account of user 819. This achieves automatic login using the ID code to identify the account, in preference over the manual entry of username 1212 and password described above. In such a case, the ID code is associated with the account of user 819 at the time the account is created.

The second use of the ID code is for rewards downloaded as files from server 180 for use in flash 147 to be encrypted in a way that is dependent upon the ID code. Whether the identifying number is unique, or merely infrequently duplicated, the result is that downloads by user 819 for use in his cartridge 140 are assured (or at least very likely) to be of no value to his friends, for use in their cartridges 140, because of mismatched ID codes. This encoding is used to mitigate the rampant piracy of rewards that might be expected if it were merely necessary to provide the files embodying one's personally earned and downloaded rewards to one's friends.

While more robust encryption techniques are well known, it is sufficient for the downloaded reward to be encoded by using the exclusive-or function, with the ID code as one of the operands and the reward data as the other. Decoding would be achieved by repeating the mathematical operation throughout the reward data. If the ID code were a 16-bit value, the operation would be performed on each 16-bit word of the reward data. If the ID code were a 64-bit value, then the operation would be repeated for each 64-bit word of the reward data. A more complex public key encryption technique could be used, but would provide only a marginally effective increase in security.

Alternatively, an ID code could be generated for each reward to be downloaded. For example, at the time an earned reward is selected for download, the corresponding earned reward record 1030 could have an ID code field (not shown) initialized with a unique or infrequently duplicated value (e.g., derived from the current value of the RTC) that would be used to encode the reward downloaded from server 180.

As the reward is loaded from server 180 or personal computer 160 into cartridge 140, the ID code is used to decode the encrypted reward, as it is being stored in flash 147. That is, the reward is stored in unencrypted, ready-to-run form. Alternatively, the reward could be stored encrypted and only unencrypted at run time.

Web page screen 1210 is hosted by server 180 and is preferably available only after user 819 has logged-in. Two main selections are provided. The first selection is option 1214, to review records of user 819 previously uploaded is accessed through button 1216. The second selection is option 1218 to selection of rewards for user 819 that have not yet been downloaded, which is accessed by button 1222.

A page (not shown) appearing in response to activation of button 1216, provides graphical displays of the user's progress in his exercise program. Such displays would preferably comprise graphs depicting improving skill, repetition counts, speed, and endurance over time. Preferably, these displays are dynamically generated for user 819 from historic exercise data 1000 previously uploaded to server 180 and stored in database 182, by means of a service running on server 180 (e.g., a CGI, ASP, or PHP program) and returned in a form suitable for a browser running on personal computer 160 and accessed through the Internet 170 in the usual manner.

In response to user 819 pressing button 1222, server 180 preferably returns reward selection page 1230. Unredeemed earned reward 1232 is an unredeemed reward from earned reward database 1020. Preferably, superior rewards are identified by levels 1233 or other value indicator to remind user 819 of the degree of effort expended to earn this reward, and to suggest that great rewards await continued diligence and/or improved performance on his part.

Rewards which user 819 can select as fulfillment of unredeemed earned reward 1232 are listed by names 1234 and 1234', and description 1236 and 1236'. Clicking on reward name 1234 would initiate a download of a file containing the reward selected. Preferably, the reward file contains an extension or MIME type such that, once downloaded, the browser passes the file to a helper application that manages the transfer of the reward file from personal computer 160 via connection 150 to exercise computer 100 and flash 147. Helper applications to which downloaded files are passed, based on extension or other property, are well known. Alternatively, the reward file can be stored on local disk 162 and transferred to flash 147 at a later time.

In an alternative embodiment, where earned reward database 1020 is not uploaded to server 180, a reward code (not shown) is revealed to user 819 in step 932 on display 124. This reward code can be entered according to instruction 1218 into field 1220, prior to pressing button 1222. In such a case, the unredeemed earned reward 1232 is specified by the reward code entered in field 1220. If an ID code is provided by the system, as previously discussed, it may either be incorporated into the reward code, or obtained during login. In such a case, the ID code will be used to encode the downloaded file for use only on machines having a matching ID code.

Another type of reward that can be offered to user 819 by the system, are coupons. In FIG. 13, a coupon 1300 is shown on display 124 after having been selected in one step 932 by user 819, and later summoned for fulfillment by user 819 in a succeeding fulfillment step 934.

Coupon 1300 contains product offer description 1302, a merchant identification 1304, and preferably, instructions 1306 to be followed by merchant employees when the coupon is used. An offer represented in coupon 1300 has been negotiated by prior agreement with the merchant identified by merchant identification 1304.

In an alternative embodiment, the coupon reward 1300 selected in step 932 would be downloaded to personal computer 160 and printed on a printer (not shown). Coupons downloadable via the Internet and then printed are well known. Because printed coupons can be easily duplicated, if the merchant wishes to limit the number of coupons provided to user 819, then each downloaded coupon contains unique indicia, such as a barcode, which can be examined by the merchant's point-of-sale register to ensure that a given downloaded coupon is only redeemed once.

In the preferred embodiment, the downloaded coupon is transferred to exercise computer 100. As previously discussed, this reward file can be locked so that the correct ID code is required for the file to be usable.

Per agreement with the associated merchant, coupon reward 1300 will be available for downloaded from server 180 only for a particular time. Further, the resulting earned rewards record 1030 will have an expiration date stored in field 1036, after which the coupon cannot be used in step 934, even though the reward has already been downloaded.

Instructions 1306 direct the merchant's cashier to press button 127. Thereafter, display 124 will display further instructions (not shown) for executing the transaction offered to user 819 in description 1302. Typically, the further instructions will include a discount code (not shown) that is predetermined by the merchant and programmed into the merchant's point-of-sale registers to automatically call up the correct discount when entered by the cashier. Such discount codes are well known. When the transaction is concluded, a final push of a button (e.g. 127') by the cashier will set expired flag 1037 and the coupon is no longer available to user 819, it has been used.

If the agreement with the merchant allows coupon 1300 to be re-used by user 819, renewable flag 1034 will be set and renew date 1035 will contain an interval. For example, if a coupon is specified to be redeemable once per week by a user 819, then at the time the coupon 1300 is exercised and expired flag 1037 is set by the cashier, the date awarded field 1032 will be set to one week from the current date read from RTC 144. When the week has passed, coupon 1300 will again be available to user 819 in step 934.

The reason that such coupons are contemplated as rewards is that, for some individuals, products from certain merchants, especially foods and beverages, are known to be extremely enticing. In moderation and in conjunction with having motivated an appropriate amount of exercise, even the richest dessert can produce a "healthy" net outcome. However, coupon 1300 is not limited to food, but can be for any product (e.g. toys, music CD) or service (e.g. theme park admission, movie tickets) which provides motivation to user 819 and for which a sponsoring merchant is available.

With downloadable rewards, such as the games, video, and coupons mentioned above, there is an issue as to how the operator of server 180 can afford to provide user 819 with an unlimited number of rewards. It is unlikely that a single purchase price for cartridge 140 will adequately support such a business.

The provision of coupon 1300 as a reward may be considered advertising for the associated merchant. If the merchant is charged a fee for this advertising, the resulting revenue for the operator of server 180 may merely cover the expenses of providing the coupon, or may represent a sponsorship of other downloadable rewards.

Games, video, and music provided as downloadable rewards may need to be purchased or licensed from their third-party owners, prior to those rewards being provided for download on server 180.

The reason that earned rewards database 1020 is preferably uploaded to database 182 is now clear: a license for a non-coupon downloadable reward may require a royalty payment to a third-party owner of the reward. Further, advertising fees charged to a merchant may be based on the number of coupon downloads or consummated product transactions made as a result of a downloaded coupon.

A preferable way to support an unlimited, downloadable rewards embodiment, is to offer a subscription service to user 819. Since in many cases, user 819 will be a child, such a subscription would often be arranged by the user's parents. An appropriate periodic (e.g. monthly) fee would generally cover the expenses of providing the downloadable rewards for the specified period.

In the subscription service embodiment, a report 1410 is provided to the parents of user 819 to reassure the parents that user 819 is making good use of the subscription. This allows the parents to conveniently monitor and commend their child's activity with wearable exercise computer 100, or if user 819 has been lax, it allows the parents to encourage increased use of exercise computer 100.

Though report 1410 could be made available by server 180 to a browser running on personal computer 160 via the Internet 170, not every parent would remember to regularly review the progress of user 819. For this reason, it is preferable for report 1410 to be delivered via mail, addressed to the parent 1412. Parent name 1412 and the appropriate mailing address is preferably entered at the time the account of user 819 is established.

Report 1410 preferably includes a summary of reward utilization 1414 by user 819, a summary of progress 1418. To give busy parents a complete idea of the kinds and levels of activities involved, a table of exercises 1416 may be provided, including for each exercise, the number of daily repetitions, the difficulty class, and skill level exhibited by user 819. Preferably, a table of rewards 1420 is also given, to inform the parents of the value received by user 819 in using the system. Table of rewards 1420 also makes parents aware of coupons earned by user 819, which is especially important if they have upcoming expiration dates. By observing in report 1420 that user 819 has a coupon requiring a trip to a specific merchant, parents can become actively involved in the reward mechanism, further motivating user 819 to exercise.

In an embodiment where cheating behaviors are detectable, report 1410 may include a notice (not shown) when cheating behaviors have been detected. Such a notice would prompt the parents to speak with user 819 about the inappropriateness of such attempts and discourage further cheating attempts.

Report generation from databases, for reports such as report 1410 and databases such as databases 1000 and 1020, is a well-known activity in modern business information processing.

Figure 15:
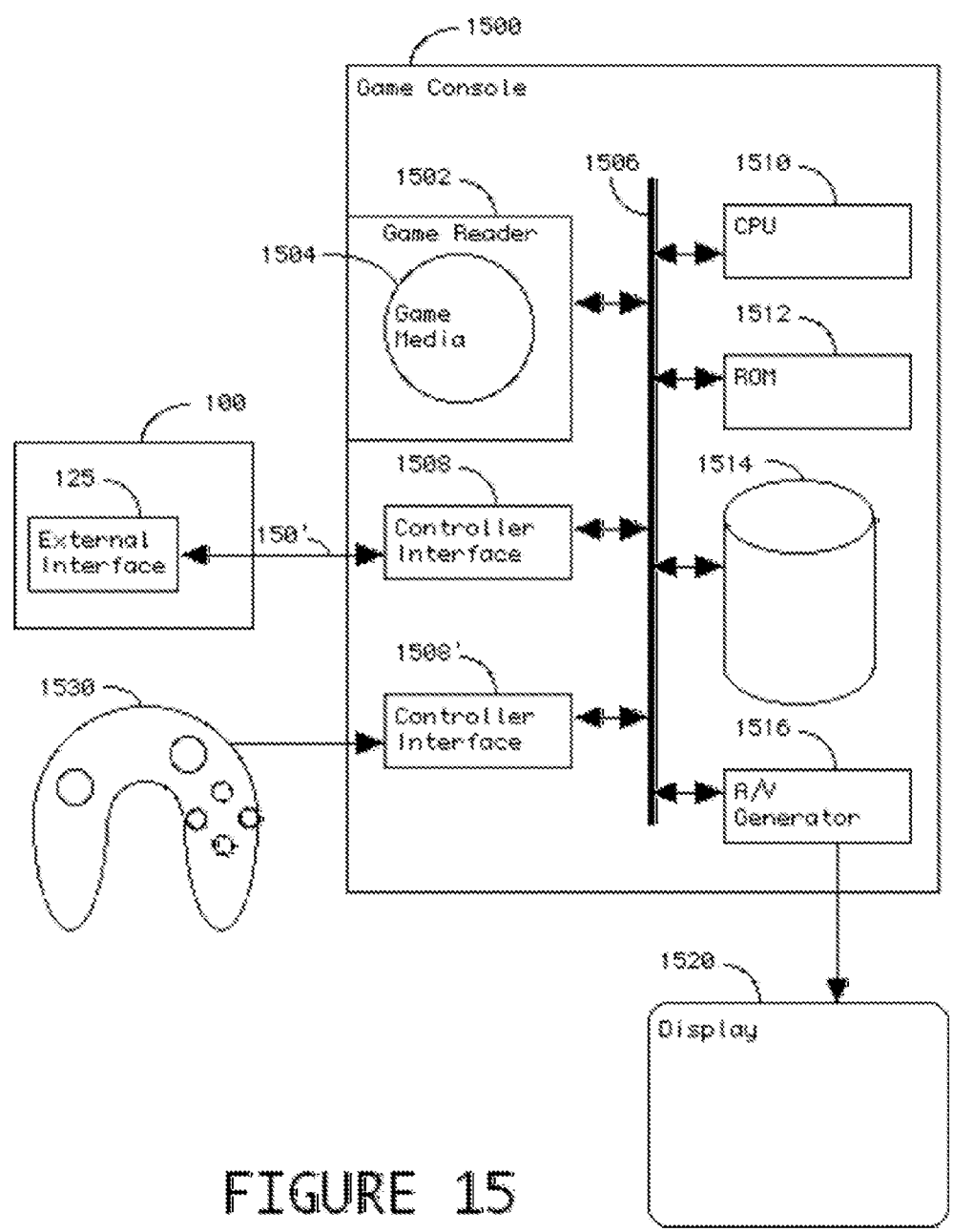
FIG. 15 is a block diagram of an alternative embodiment where the exercise computer mediates access to a video game console.

FIG. 15 shows an alternative embodiment, wherein playing a game as a reward for exercises completed does not occur on wearable exercise computer 100, but occurs instead on game console 1500.

Game console 1500 has a game reader 1502 for reading game media 1504. Typically, game media 1504 is a cartridge or a CD-ROM for which game reader 1502 would take the form of a receptacle or a CD-ROM drive, respectively. While the computer architecture for a specific game console may take many well-known forms, the following is illustrative. A bus 1506 interconnects CPU 1510 with game reader 1502 and each of the other elements of the console. ROM 1512 is used to boot the system and provide baseline functionality for the console. Preferably, some form of non-volatile storage is available, such as disk 1514, though NVRAM (not shown) could also be used. Audio and video generation is provided by A/V generator 1516, and used to drive display 1520, which includes speakers for audio (not shown).

Game consoles are typically controlled by game controller 1530, shown plugged into controller interface 1508'. Well known in the prior art, controller 1530 is manipulated by the user. Signals from controller 1530 are received by controller interface 1508' and made available to CPU 1510 to operate the user interface, which is directed by software in ROM 1512 and, when game media 1504 is loaded, by software on game media 1504. RAM (not shown), is used by CPU 1510 for recording variables, and in the case of disk-based game media, for holding an executable copy of software from game media 1504.

For this embodiment of the invention, wearable exercise computer 100 is connected to game console 1500, for example to controller interface 1508 via adapter 150' from external interface 125. Software, preferably in ROM 1512, is responsive to communication from exercise computer 100 through controller interface 1508.

Alternatively, the software responsive to communication from exercise computer 100 may reside on game media 1504, or be loaded from disk 1514.

A reward selected in step 932 and communicated to game console 1500 in step 934 enables game play on game console 1500. Such a reward may be of the form "n minutes of play", "n lives" or "unlimited play for 48 hours from the time of the last exercise session", or another measure of game play, where 'n' is preferably a function of the user's exercise performance (e.g. better performances relative to the targets result in larger values of 'n').

The reward communicated to game console 1500 in step 934 is preferably stored on disk 1514 or other storage within console 1500 or on controller 1530 (some well known controllers include NVRAM or flash memory, not shown). Software, either in ROM 1512 or on game media 1504, instructs CPU 1510 to look for a current stored reward before beginning or continuing a game. In an alternative embodiment, internal storage is not used, and communication with exercise computer 100 results in an examination of a reward in earned reward database 1020 in situ on exercise computer 100.

Preferably, the software requiring a reward before a game may be played on console 1500 is located in ROM 1512. In some present game console systems, for example the X-Box™ by Microsoft Corporation of Redmond, Wash., a parental control option is presently offered. The Entertainment Software Rating Board (ESRB) provides guidelines for game manufacturers for assigning ratings to their games. For example, the rating "T" for Teen is appropriate for games having content that may be suitable for persons ages 13 and older. "Teen" rated games may contain violent content, mild or strong language, and/or suggestive themes. On the X-Box™, a parent can select the maximum ESRB rating that they will allow to be played. Their selection is password protected, and stored on a disk internal to the X-Box™. Software in the X-Box console disallows a game having an ESRB rating in excess of the parental selection from running.

A similar mechanism can be employed to allow parents to select whether or not game console 1500 allows games to be run absent an appropriate reward. Many variations of this parental selection can be provided, including allowing unlimited, time limited, or no game play, absent a reward from exercise computer 100.

In an alternative embodiment (not shown), exercise computer 100 or adapter 150' may be interposed between game controller 1530 and game console 1500. In this configuration, exercise computer 100 will prevent the use of game controller 1530, and thereby playing of games on console 1500, unless an appropriate reward is available.

Rewards such as video, music, or computer games, delivered by devices external to exercise computer 100 (analogous to video games delivered by game console 1500) can be moderated by the present invention, and merely require an appropriately adapted external device (e.g. television, set-top box, MP3 player, boom box, PC, etc.) and the appropriate adapter to communicate between exercise computer 100 and the external device—which can include wireless and infrared connections, as well as the wired connections shown above. The implementation details of such external devices, whose normal operation is inhibited when lacking a current reward from exercise computer 100, is within the capability of ordinary skill in the art, given the examples presented herein.

The preferred embodiment is discussed in the context of a wearable exercise computer, which is able to deliver rewards to a user for exercising, the rewards coming from either an internal or external source. An alternative embodiment is discussed, showing that rewards can be delivered by an external device.

The particular implementations described, and the discussions regarding details, and the specifics of the figures included herein, are purely exemplary; these implementations and the examples of them, may be modified, rearranged and/or enhanced without departing from the principles of the present invention. In particular, the computer architectures, data structures, and flowcharts herein are exemplary, and significant alteration can be made without departing from the spirit of the invention.

Particular features of user interface, for web site, PC software, and the exercise computer, and the capabilities of the databases, will depend on the architecture used to implement a system of the present invention, the operating systems of the servers and client computers selected, and the software code written both for the servers and client computers. It is not necessary to describe the details of such programming to permit a person or team of ordinary skill in the art to implement the application, user interface and services suitable for implementing a system within the scope of the present invention. The details of the software design and programming necessary to implement the principles of the present invention are readily understood from the description herein.

Various additional modifications to the embodiments of the invention, specifically illustrated and described herein, will be apparent to those skilled in the art, particularly in light of the teachings of this invention. Further, it will be apparent that the functionality of this invention can be incorporated into and function from within the context of other products, including an e-commerce system. It is intended that these cover all modifications and embodiments that fall within the spirit and scope of the invention. Thus, while preferred embodiments of the present invention have been disclosed, it will be appreciated that it is not limited thereto but may be otherwise embodied within the scope of the following claims.

I claim:

1. A method for motivating a user to exercise, comprising the steps of:
    (a) providing a program for a first computer, said first computer having communication with a sensor, said program able to recognize each performance of a first exercise by the user of a plurality of exercises through the sensor;
    (b) automatically recognizing a first performance of the first exercise with said program;
    (c) automatically making a first record with said program in response to the first performance;
    (d) repeating at least steps (b) and (c) a plurality of times; and,
    (e) providing a report of progress by the user based on the records.

2. The method of claim 1, wherein step (b) consists of finding a correspondence between a predetermined pattern associated with the first exercise and an interval of readings of the sensor.

3. The method of claim 2, wherein the sensor is a plurality of accelerometers and readings of the sensor are affected by at least one of orientation and motion.

4. The method of claim 1, further comprising the steps of:
(f) automatically recognizing with said program a failed attempt to perform the first exercise; and,
(g) providing with said program at least one of advice and encouragement appropriate to overcoming the failed attempt in the future.

5. The method of claim 4, further comprising the step of:
(h) prescribing the first exercise with said program.

6. The method of claim 1, further comprising the steps of:
(f) automatically recognizing with said program a failed attempt to perform the first exercise; and,
(g) automatically making a second record with said program in response to the failed attempt;
wherein the report is further based on the second record.

7. The method of claim 1, further comprising the steps of:
(f) uploading the records to a second computer, said second computer programmed to provide a report of progress based on said records; and,
wherein (e) is performed with said second computer.

8. The method of claim 1, further comprising the step of:
(f) prescribing the first exercise with said program.

9. The method of claim 1 in which the program is further able to recognize each performance of a second exercise of the plurality of exercises, the second exercise different from the first exercise, and further comprising the steps of:
(f) automatically recognizing a second performance of the second exercise with said program; and,
(g) automatically making a second record with said program in response to the second performance;
wherein the report is further based on the second record.

10. The method of claim 1 in which the first record comprises a count of performances of the first exercise.

11. A system for monitoring exercise, the system comprising:
a sensor; and,
a first computer having communication with the sensor, said first computer having a program to automatically recognize each performance of a first exercise by a user of a plurality of exercises through the sensor and respond by producing a first record that the first exercise was performed, said program further operable to make available a report on the basis of the first record;
whereby the report indicates the user has performed the first exercise.

12. The system of claim 11, wherein the program compares readings from the sensor to a predetermined pattern indicative of the first exercise and automatically recognizes that the first exercise was performed when a substantial match is found.

13. The system of claim 12, wherein the sensor comprises a plurality of accelerometers.

14. The system of claim 11, wherein the first computer further comprises a user interface, and said program is further able to recognize a failed attempt to perform the first exercise and provide in response, through the user interface, at least one of advice and encouragement appropriate to overcoming the failed attempt in the future.

15. The system of claim 11, wherein the first record is one of a plurality of records, said system further comprising:
a display of information based on the plurality of records, whereby the progress of the user is shown.

16. The system of claim 15, wherein the display comprises a second computer at least occasionally in communication with the first computer, to which the plurality of records are uploaded, wherein the report is provided by the second computer on the further basis of the plurality of records.

17. The system of claim 11, further comprising a display driven by the first computer, to prescribe the first exercise.

18. The system of claim 11, further comprising an audio output driven by the first computer, to prescribe the first exercise.

19. The system of claim 11, in which the program will further automatically recognize each performance of a second exercise of the plurality of exercises, the second exercise different from the first exercise, and respond by producing a second record that the second exercise was performed; and wherein the report is made available on the further basis of the second record.

20. The system of claim 11, in which the first record comprises a count of performances of the first exercise.

21. A method for motivating a user to exercise, comprising the steps of:
(a) providing a computer, said computer having a program to monitor a sensor and recognize each performance of a first exercise by the user of a plurality of exercises;
(b) automatically recognizing with said computer a first performance of the first exercise;
(c) automatically making a first record of the first performance with said computer; and,
(d) providing with the computer a report based on the first record;
whereby the user's exercise performance is represented in the report.

* * * * *